(12) United States Patent
Just et al.

(10) Patent No.: US 10,006,903 B2
(45) Date of Patent: Jun. 26, 2018

(54) NUMBER OF IL4 AND/OR IL13 SECRETING T-CELLS AS A BIOMARKER FOR ALLERGIC DISEASES

(71) Applicants: INSTITUT NATIONAL DE LA SANTE ET DE LA RECHERCHE MEDICALE (INSERM), Paris (FR); UNIVERSITE PARIS DESCARTES, Paris (FR); ASSISTANCE PUBLIQUE—HOPITAUX DE PARIS, Paris (FR); UNIVERSITE PIERRE ET MARIE CURIE—PARIS 6, Paris (FR)

(72) Inventors: Jocelyne Just, Paris (FR); Benedicte Michaud, Paris (FR); Jean-Francois Bach, Paris (FR); Lucienne Chatenoud, Paris (FR)

(73) Assignees: INSTITUT NATIONAL DE LA SANTE ET DE LA RECHERCHE MEDICALE (INSERM), Paris (FR); UNIVERSITE PARIS DESCARTES, Paris (FR); ASSISTANCE PUBLIQUE—HOPITAUX DE PARIS, Paris (FR); UNIVERSITE PIERRE ET MARIE CURIE—PARIS 6, Paris (FR)

( * ) Notice: Subject to any disclaimer, the term of this patent is extended or adjusted under 35 U.S.C. 154(b) by 234 days.

(21) Appl. No.: 14/337,826

(22) Filed: Jul. 22, 2014

(65) Prior Publication Data

US 2015/0024421 A1    Jan. 22, 2015

Related U.S. Application Data

(63) Continuation-in-part of application No. PCT/IB2014/058499, filed on Jan. 23, 2014.

(30) Foreign Application Priority Data

Jan. 23, 2013  (EP) .................................. 13305079

(51) Int. Cl.
*A61K 39/00* (2006.01)
*A61K 39/35* (2006.01)
*A61K 39/36* (2006.01)
*A61K 39/38* (2006.01)
*C07K 1/00* (2006.01)
*C07K 14/00* (2006.01)
*C07K 17/00* (2006.01)
*G01N 33/50* (2006.01)
*G01N 33/68* (2006.01)

(52) U.S. Cl.
CPC ....... *G01N 33/505* (2013.01); *G01N 33/6869* (2013.01); *G01N 2333/5406* (2013.01); *G01N 2333/5437* (2013.01); *G01N 2800/24* (2013.01)

(58) Field of Classification Search
None
See application file for complete search history.

(56) References Cited

U.S. PATENT DOCUMENTS

2004/0115744 A1* 6/2004 Jakobson ............. G01N 33/505
435/7.21

OTHER PUBLICATIONS

Gabrielsson et al. Specific immunotherapy prevents increased levels of allergen-specific IL-4 and IL-13-producing cells during pollen season. Allergy 56:293-300, 2001.*
Schmittel et al. 'Application of the IFN-g ELISPOT assay to quantify T cell responses against proteins.' J. Immunol. Methods. 247:17-24, 2001.*
U-CyTech BV 'Addendum ELISPOT assay.' Published Nov. 3, 2010    https://www.ucytech.com/sites/default/files/manuals/Addendum%20ELISPOT.pdf.*
Sommer et al. Type IV hypersensitivity reactions to natural rubber latex: results of a multicentre study. Brit. J. Derm. 146:114-117, 2002.*
Greer et al. 'Literature review on Latex-Food Cross-Reactivity 1991-2006.' Dec. 4, 2007. http://latexallergyresources.org/sites/default/files/attachments/Latex-food%20cross-reactivity%20review.pdf.*

* cited by examiner

*Primary Examiner* — Nora Rooney
(74) *Attorney, Agent, or Firm* — Whitham, Curtis & Cook, P.C.

(57) ABSTRACT

The present invention relates to an in vitro use of a number of IL-4 and/or IL-13 secreting T-cells as a biomarker for diagnosing and/or monitoring an IgE-dependent allergic disease.

10 Claims, 7 Drawing Sheets

NUMBER OF IL4 AND/OR IL13 SECRETING T-CELLS AS A BIOMARKER FOR ALLERGIC DISEASES

FIELD OF THE INVENTION

Figure 1:
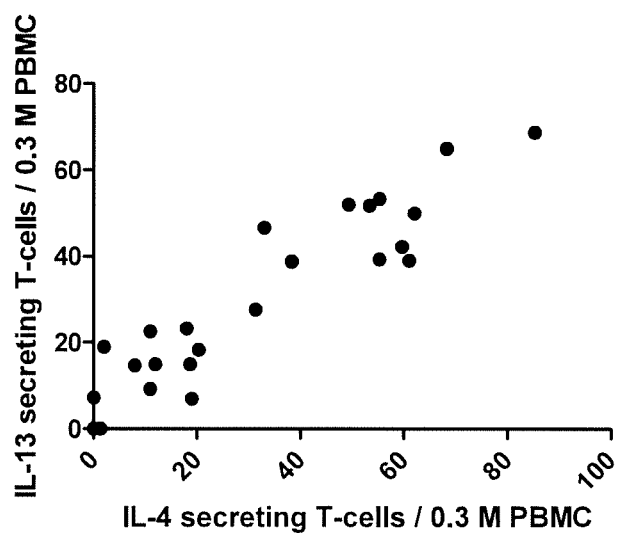

The present invention relates to the field of biomarkers for IgE-dependent allergic diseases. In particular, the invention concerns uses, methods and kits implementing novel biomarkers for diagnosing and/or monitoring an allergic disease.

More particularly, the invention relates to a number of interleukin (IL) secreting T-cells as a biomarker for allergic diseases.

BACKGROUND OF THE INVENTION

Routinely, atopic diseases are allergic diseases, which can be divided in different categories, such as airborne allergies, food allergies and insect allergies, among others. The prevalence of allergic diseases is regularly increasing worldwide and represents a significant public health issue, especially in industrialized countries. For example, worldwide statistics from the American Academy of Allergy Asthma and Immunology shows for example that: allergic rhinitis affects between 10% and 30% of the population; insect (bees, wasps, fire ants) allergy fatal reactions occur in up to 50% of individuals who have no documented history of a previous systemic reaction; hive reaction occurs with lifetime prevalence above 20%.

The physiopathology underlying the allergic diseases described above involves immediate hypersensitivity reactions characterized by the production of IgE antibodies to the triggering allergen(s). These atopic or allergic reactions are thus defined as IgE-dependent. IgE-dependent allergic diseases are most often of respiratory origin, the allergens being airborn, such as pollen, house dust mite, animal fur, or of alimentary origin. Allergen-specific IgEs will bind to specific receptors on basophils and mastocytes that localize within the target tissue and, upon encounter with the allergen will liberate the contents of their granules and precipitate the allergic symptoms (Delespesse, 2012). Atopic diseases are also characterized by the involvement of adaptive immune responses that include Th2 lymphocytes, specific of the allergen(s) producing IL-4, IL-5 and IL-13.

Atopic diseases may be clearly distinguished from another clinical situation, whose underlying physiopathological mechanisms are totally distinct, that is delayed hypersensitivity. Examples of delayed hypersensitivity reactions are skin (or contact) allergic diseases and allergic diseases to different drugs. These delayed hypersensitivity reactions are IgE-independent. In hypersensitivity reactions the allergen is often a hapten. An IgE-independent allergic disease is characterized by the fact that the immunity response is indirect, since the hapten needs to be coupled to another cellular component from the host, usually a protein, in order to elicit an allergic reaction (Bach, 2012). In addition, another major physiopathological difference is that, delayed hypersensitivity reactions do not involve Th2 lymphocytes but rather Th1 lymphocytes that produce IL-2 and Interferon (IFN)γ.

To date, allergen immunotherapy is the only specific treatment that cures the underlying allergic disorder. Treating allergy, it also allows the improvement of pre-existent allergic condition, for example asthma and prevents the development of new sensitizations.

Nevertheless, allergic polysensitization is a frequent phenotype of allergic diseases, such as, for example, asthma. Therefore, the importance of defining exactly the major allergen responsible of allergic symptoms before starting specific immunotherapy is essential. Moreover, there is a special interest in monitoring the severity of the allergic disease to provide an adapted treatment.

Currently, in vivo provocation tests are among the gold standards for diagnosis the occurrence of an allergic disease. A provocation test consists in exposing an individual to a suspicious allergen at increasing doses and monitoring the body's functions.

Numerous provocation tests are available and were described in the literature. Among them, bronchial provocation test, nasal provocation test, oral provocation test and skin provocation test are of special interest.

Skin provocation tests or skin allergy tests are widely used. These tests comprise intradermal (skin prick test) administration into the skin (usually the fore harm or the back) of very small quantities of an allergen in order to visualize directly an allergic reaction on the skin.

The non-specific bronchial provocation test is used to detect asymptomatic allergic asthma or to diagnose occupational asthma. In routine, the patient is exposed to a broncho-constrictor agent, usually a non-specific one such as histamine or methacholine. Following this exposure, the body's respiratory function is assessed by using a spirometer to measure the changes in the forced expiratory volume in one second, reflecting changes in lung function.

The specific bronchial provocation test and nasal provocation test, in which suspected allergens are administered, are the gold standards for diagnosis of, for example, mite allergy, but not routinely applied.

Following the same concept, the allergen can be provided to a patient throughout an oral administration to detect a food allergy. This is, for example, the case of cow's milk allergy in children.

Effectively, these provocation tests are invasive, require a qualified physician, are costly because of sophisticated materials, and most importantly may present risks, such as the occurrence of severe asthma exacerbation (for asthma) or anaphylaxis (for food allergy).

Hence, because they present well known risks, these tests are currently mainly used in clinical research within a hospital environment.

In vitro immunological tests routinely used are the determination of specific immunoglobulin E (IgE) that is indicative of the sensitization to an allergen but cannot allow the allergen to be identified. Moreover, increasing of IgE amount in IgE-dependent allergic diseases is often very limited, and therefore represents a poor biomarker for diagnosis.

The only functional test currently available is the basophil activation test (BAT), which relies upon quantification of alterations of specific activation markers on the surface or inside the basophil cells by flow cytometry. These changes can be detected and quantified on a single-cell basis using specific monoclonal antibodies coupled to a fluorochrome. However, this test has a low sensitivity and requires a divalent antigen, impairing its use for the diagnosis and/or monitoring of drug allergies.

In the field of IgE-independent allergic diseases, WO 02/073195 describes an in vitro test for diagnosing a nickel contact allergy. This test relies upon detecting cytokines that are released by T-cells after a hapten, nickel, has contacted said T-cells.

However, in the field of IgE-dependent allergic diseases there is still a need for a biomarker allowing the diagnosing or the monitoring of an allergic disease in an easy, sensitive, reproducible, and cost-effective manner.

Also, there is a need for a biomarker allowing the diagnosing or the monitoring of an IgE-dependent allergic disease and the determination of which being safe and non-invasive for patient.

There is a need of a biomarker, the determination of which being able to be correlated with the intensity of the symptoms associated with an IgE-dependent allergic disease.

In the field of IgE-dependent allergic disease diagnosing and/or monitoring, there is also a need to provide a biological test that is safe for the patient.

Moreover, there is a need to provide a biological test that is not invasive.

There is also a need to provide a biological test that is specific for a well-defined allergen able to elicit an IgE-dependent reaction.

There is also a need to provide a biological test that is cost effective, easy and rapid to execute.

In addition, there is a need to provide a biological test that is suitable for different categories of IgE-dependent allergic diseases or different allergens able to elicit an IgE-dependent reaction.

There is a need to provide a biological test that does not induce an anaphylactic reaction.

Finally, there is fundamental need to develop a biological test to diagnose and/or to monitor the severity of the condition of an IgE-dependent allergic disease.

SUMMARY OF THE INVENTION

The present invention has for purpose to meet those needs.

According to one of its objects, the invention relates to a use of a number of IL-4 and/or IL-13 secreting T-cells as a biomarker for IgE-dependent allergic disease, and in particular for diagnosing and/or monitoring an IgE-dependent allergic disease.

Indeed, the inventors have unexpectedly observed that the number IL-4 and/or IL-13 secreting T-cells can be correlated with the severity of an IgE-dependent allergic disease. Accordingly, the evaluation of this number of IL-4 and/or IL-13 secreting T-cells provides a simple and highly reproducible biological test for diagnosing and/or monitoring an IgE-dependent allergic disease. As detailed, in the Examples presented here-below, the use of the number of T-cells secreting IL-4 and/or T-cells secreting IL-13 allows the diagnosing, the monitoring and/or the predicting of risk of occurrence of an IgE-dependent allergic disease, in particular liable to be triggered by an airborne allergen such as dust house mite allergen, pollen, mold, or food allergens such as cow's milk, or peanut.

Within the invention, the term "allergen" intends to refer to an antigen able to induce, into a susceptible sensitive and responsive individual, an allergic disease. An allergen may be a purified molecule, a mix of purified molecules, an unpurified molecule or a mix of unpurified molecules, synthetic or naturally found in nature, food, drug and matter, able to elicit an allergic disease.

Within the invention the terms "allergy" or "allergic disease" are used interchangeably to designate a hypersensitivity disorder of the immune system reacting to normally harmless substances or molecules in the environment. A substance or molecule that causes an "allergy" or an "allergic disease" is called an allergen.

Within the scope of the instant invention, "allergy" or "allergic disease" encompasses exclusively the clinical situation defined as "atopy" that is an IgE-dependent allergy or IgE-dependent allergic disease.

In an individual, an IgE-dependent allergy or an IgE-dependent allergic disease may be elicited as a consequence of a contact between said individual and an allergen. Such individual may be qualified as sensitive or responsive to the given allergen. A contact between an individual and an allergen may be operated through any physical interaction of the allergen with at least a cell, a tissue, an organ from said individual, throughout any possible route, i.e. but not limited to nasal, oral, ocular, auricular, pulmonary, systemic, topical, parenteral, urogenital, rectal and intramuscular route.

According to another of its aspects, the invention relates to a use of a number of IL-4 and/or IL-13 secreting T-cells as a biomarker for screening or assessing an activity of a drug presumed effective in preventing and/or treating an IgE-dependent allergic disease.

According to another of its aspects, the invention relates to a method for diagnosing an IgE-dependent allergic disease to an allergen, in an individual, said method comprising at least the steps of:

(a) contacting, with an allergen, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

According to another of its aspects, the invention relates to a method for monitoring an IgE-dependent allergic disease to an allergen, in a previously diagnosed individual, said method comprising at least the steps of:

(a) contacting, with said allergen, an isolated biological sample from said individual, said sample comprising T-cells, in conditions suitable for said T-cells to secrete IL-4 and/or IL-13; and (b) measuring a number of IL-4 and/or IL-13 secreting T-cells.

According to another of its aspects, the invention relates to a method for screening a drug presumed effective in preventing and/or treating an IgE-dependent allergic disease, comprising at least the steps of:

(a) treating at least one population of T-cells able to secrete IL-4 and/or IL-13 with said drug, said population of T-cells being contacted with an allergen inducing a secretion of IL-4 and/or IL-13, (b) measuring a number of IL-4 and/or IL-13 secreting T-cells in said treated population of T-cells.

According a preferred embodiment, in a method or a use according to the invention, a measured number of IL-4 and/or IL-13 secreting T cells may be compared, for example, in a further step, with a reference value. According to the case, a deviation observed between a number of IL-4 and/or IL-13 secreting T cells and a reference value may indicative of, or informative on, an IgE-dependent allergic disease, or may be indicative of an efficacy of therapeutic treatment or of a screened drug.

According to another of its aspects, the invention relates to a method for assessing an activity of drug presumed efficient for preventing and/or treating an IgE-dependent allergic disease in an individual treated with said drug, comprising at least the steps of:

(a) measuring a number of IL-4 and/or IL-13 secreting T-cells, in a first isolated biological sample from said individual before a treatment with said drug and in a second isolated biological sample from said individual after a treatment with said drug; and (b) determining if said number of IL-4 and/or IL-13 secreting T-cells is decreased in the first biological sample obtained after the treatment as compared to the second biological sample obtained before the treatment;

wherein a decreased number of IL-4 and/or IL-13 secreting T-cells in the second sample relative to the first sample is indicative of an activity of said drug.

According to a preferred embodiment, in a step of measuring a number of IL-4 and/or IL-13 secreting T-cells in a method in accordance with the invention, a number of T-cells secreting IL-4 and a number of T-cells secreting IL-13 may be measured.

According to another embodiment, the invention relates to a method to monitor desensitization to an allergen able to elicit an IgE-dependent allergic disease in an individual in need thereof, comprising measuring a number of IL-4 and/or IL-13 secreting T-cells in a biological sample isolated from said individual after administration of a desensitization treatment, and comparing the measured number to a number of IL-4 and/or IL-13 secreting T-cells measured in biological sample isolated from said individual before administration of the desensitization treatment.

The uses and methods according to the invention may be carried out in vivo, in vitro or ex vivo. Preferably, they are carried out in vitro.

According to another of its aspects, the invention relates to kit for diagnosing and/or monitoring an IgE-dependent allergic disease, said kit comprising:

(a) at least a composition comprising antibodies directed against IL-4 and/or IL-13;

(b) at least an compound known to stimulate IL-4 and/or IL-13 T cells secretion; and (c) at least a mean for detecting IL-4 and/or IL-13 antibodies.

The invention has for advantages to provide a simple, cost-effective, and reliable assay to diagnose or monitor an IgE-dependent allergic disease.

According to another of its advantages, the invention allows for monitoring a therapeutic treatment presumed effective for preventing or treating an IgE-dependent allergic disease or for screening drug candidate presumed effective for preventing or treating an IgE-dependent allergic disease.

According to another of its advantages, the invention allows for specifically diagnosing or monitoring the effects of a specific allergen in an IgE-dependent allergic disease.

LEGENDS OF THE FIGURES

FIG. 1: illustrates a correlation diagram between the number of IL-4 secreting and IL-13 secreting house dust mite specific T-cells in response to house dust mite.

Figure 2:
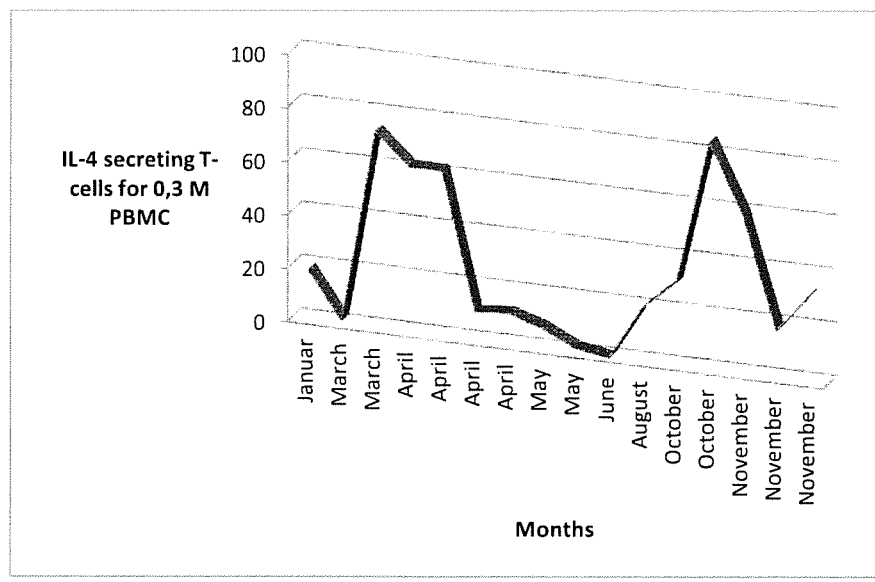

FIG. 2: illustrates that the number of IL-4 secreting house dust mite specific T-cells fluctuates with the seasons, since two peaks, one in the fall and one in early spring, are observed.

Figure 3:
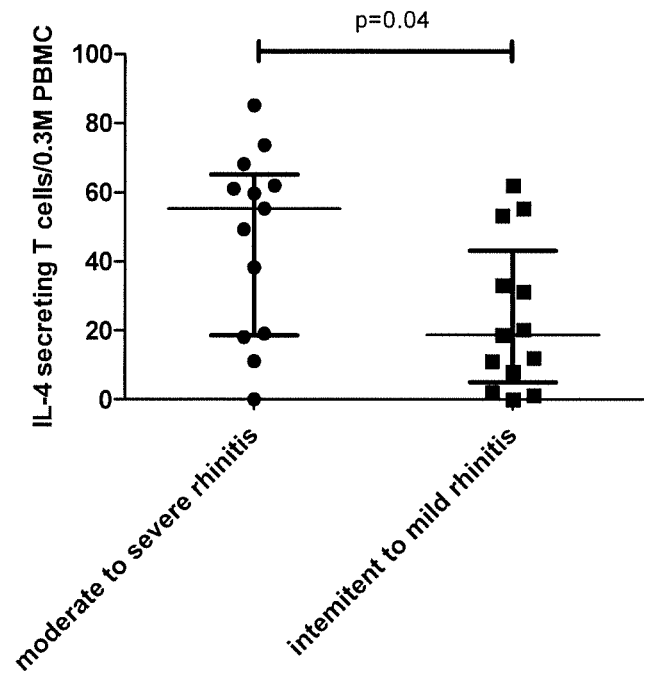

FIG. 3: illustrates the variation of the number of IL-4 secreting house dust mite specific T-cells with respect to the severity of allergic rhinitis.

Figure 4:
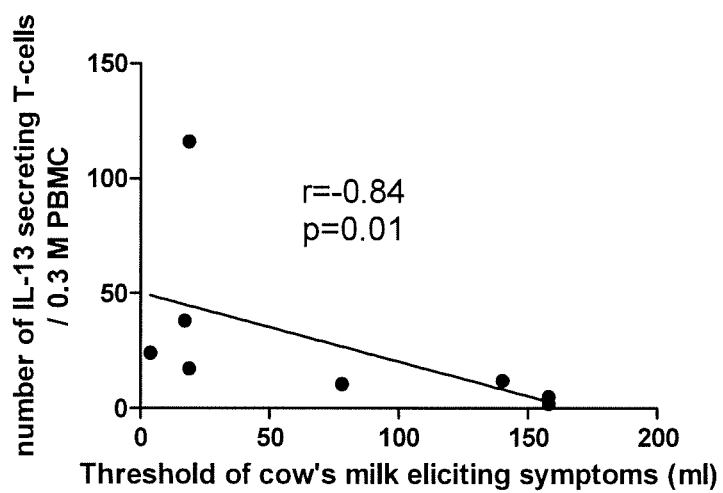

FIG. 4: illustrates the number of IL-13 secreting cow's milk casein specific T-cells as a function of the cumulative reactive dose of ingested cow's milk.

Figure 5:
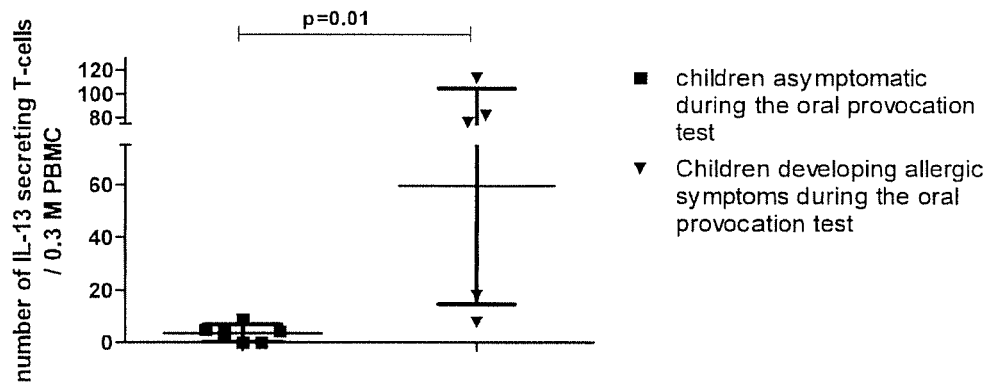

FIG. 5: illustrates the number of IL-13 secreting peanut specific T-cells as a function of the existence of an allergic response during an oral provocation test.

Figure 6A:
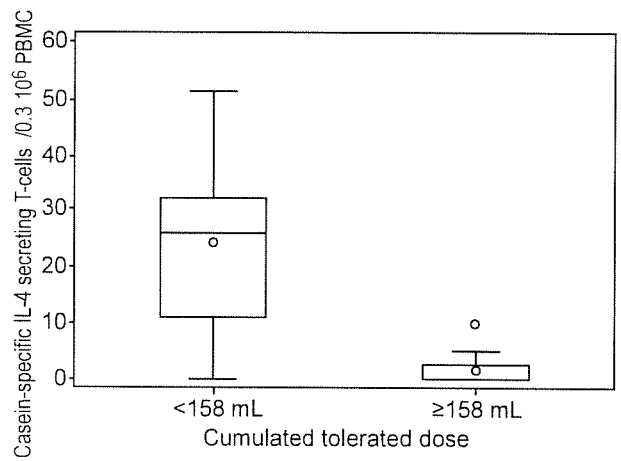
Figure 6B:
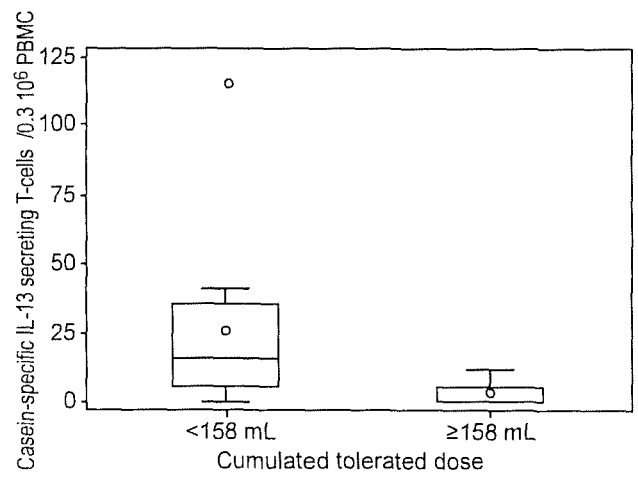

FIG. 6A-B: illustrates a correlation diagram between the cumulative tolerated dose and ELISpot test results. A. Number of IL-4 secreting T-cells. B. Number of IL-13 secreting T-cells. Left panels represent cow's milk allergic individuals. Right panels represent cow's milk non-allergic individuals.

Figure 7:
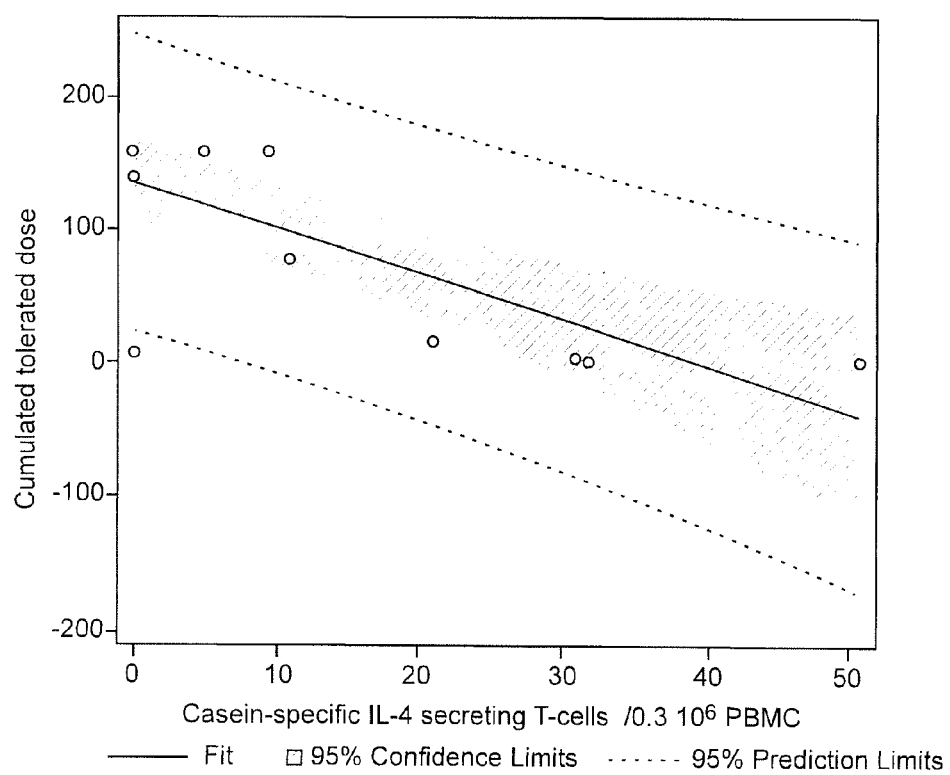

FIG. 7: illustrates a correlation diagram between the number of casein-specific IL-4 secreting T-cells per $0.3 \times 10^6$ PBMC and the cumulative tolerated dose.

Figure 8A:
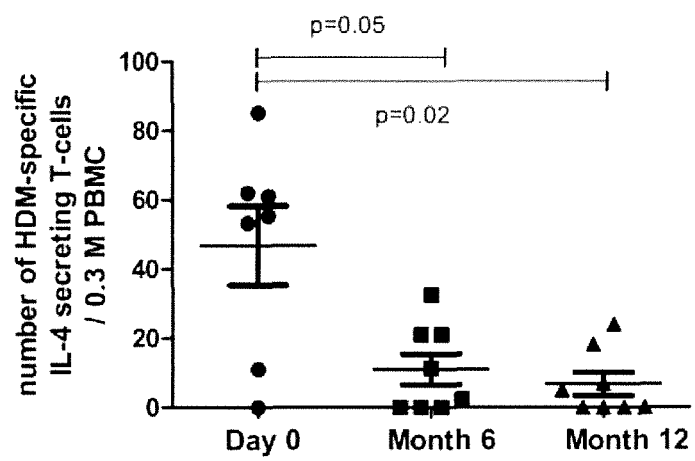
Figure 8B:
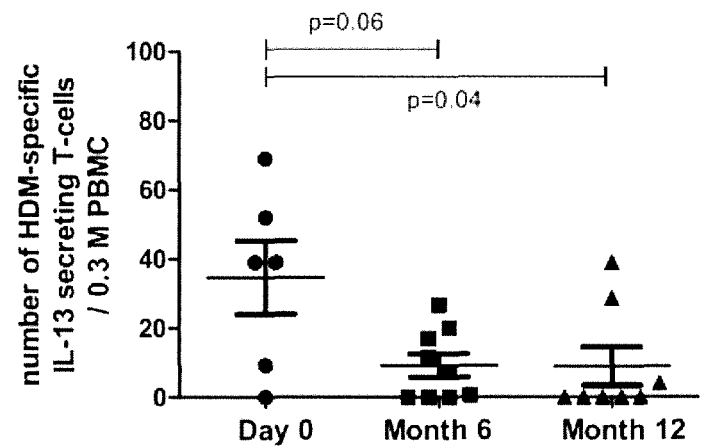

FIG. 8A-B: illustrates the number of house dust mite specific IL-4 (A) or IL-13 (B) secreting T-cells at 6 or 12 months after the start of immunotherapy (day 0).

Figure 9A:
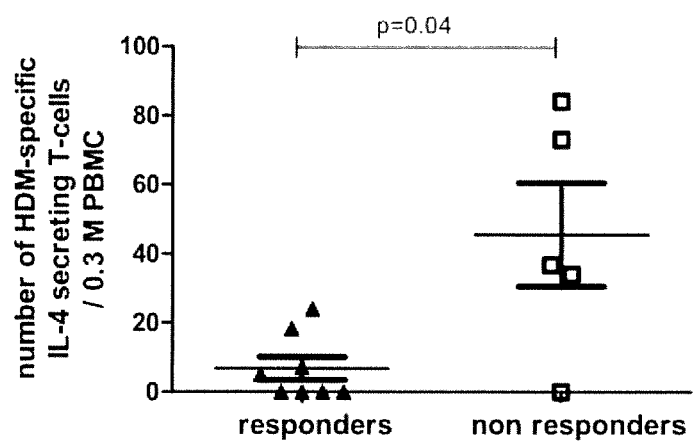
Figure 9B:
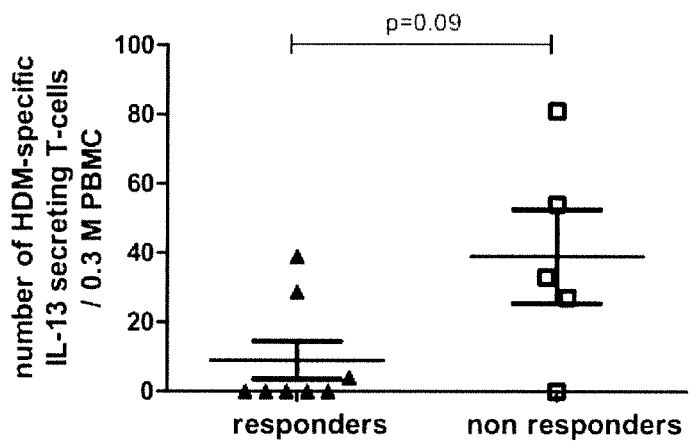

FIG. 9A-B: illustrates the number of house dust mite specific IL-4 (A) or IL-13 (B) secreting T-cells respectively in individuals responding to immunotherapy (responders; left panels) and in individuals not responding to immunotherapy (non-responders; right panels).

DESCRIPTION OF THE INVENTION

Uses and Methods

The uses and methods of the invention implement as a biomarker the number of IL-4 and/or IL-13 secreting T-cells. This biomarker allows for diagnosing or monitoring an IgE-dependent allergic disease in response to a specific allergen in an individual, as well as for assessing the efficiency or screening a drug presumed efficient against an IgE-dependent allergic disease.

In one of its aspect, the invention relates to a method for diagnosing and/or monitoring an IgE-dependent allergic disease to an allergen, in an individual, said method comprising at least the steps of:

(a) contacting, with an allergen, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

An "individual" or a "patient" considered within the present invention may be any subject comprising sensitive T-cells liable to secret a cytokine IL-4 or IL-13 in response to an allergen. Preferably, an individual may be a mammal, and more preferably an animal of economic importance, for example farms, laboratories or food industries animals, such as sheep, swine, cattle, goats, dogs, cats, horses, poultry, mice, rats. Also, an individual according to the invention may be a human. And more preferably, an individual is a human.

An "IgE-dependent allergic disease" considered within the invention may be any disease selected from the group consisting of airborne allergies, food allergies and insect allergies.

Uses and methods in accordance with the invention are preferably performed within an isolated biological sample. A "biological sample," as used herein, generally refers to a sample obtained and isolated from an individual, including sample of biological tissue or fluid origin, obtained, reached, or collected in vivo or in situ. Such samples can be, but are not limited to, organs, tissues, fractions and cells isolated from a mammal. Exemplary biological samples include but are not limited to a cell culture, a cell line, a biopsy, a tissue, oral tissue, gastrointestinal tissue, an organ, a biological fluid, a blood sample, a skin sample, and the like. Preferred biological samples include but are not limited to a blood, PBMCs, a tissue biopsy, or an oral mucosa sample and the like. The sample can be a crude sample, or can be purified to various degrees prior to storage, processing, or measurement.

An isolated biological sample of the invention comprises T-cells.

The step of collecting biological samples for the uses and methods of the invention is performed before carrying out the invention and is not a step of a use or a method in accordance with the invention.

In one embodiment, an isolated biological sample suitable for the invention comprising T-cells may be selected from the group consisting of a blood sample, a biopsy, a fluid sample, in particular a sample from a nasal lavage fluid or a bronchoalveolar lavage fluid.

In one embodiment, an isolated biological sample suitable for the invention may be an isolated whole blood sample.

The samples suitable for the invention can be purified prior to testing. In some embodiments, the blood mononuclear cells, and preferably the T-cells, can be isolated from the remaining cell contents prior to testing.

The IL-4 and/or IL-13 secreting T cells are memory T cells. As compared to naïve T-cells, one of the most valuable intrinsic features of memory T-cells is that they are able to perform rapid production of cytokines upon re-stimulation.

Naïve T-cell are unexperienced T-cell that have not encountered any antigen. When naïve T-cells are first in contact with an antigen they experience activation and proliferation (division) in order to form clones or daughter cells. A subcategory of these T-cell clones will differentiate into effector T-cells, which are intended to either produce cytokines (helper T-cells) or invoke cell killing (cytotoxic T-cells). Another subcategory of T-cells will form memory T-cells, which will be maintained in an inactive state in the host for a long period of time until they re-encounter the same antigen and reactivate. Upon re-encountering the antigen, memory T-cells rapidly and efficiently produce and secrete cytokines, providing a fast response of the host to fight said antigen.

The separating the blood mononuclear cells or the T-cells may be performed by any methods known in the art, for example by density gradient centrifugation.

According to one embodiment, when using an isolated whole blood sample, peripheral blood mononuclear cells (PBMC), comprising lymphocyte cells and monocyte cells, may be separated from plasma (non-cellular components), polynuclear cells, such as neutrophil cells and eosinophil cells, and erythrocytes.

Any known method in the art to separate peripheral blood mononuclear cells (PBMC) from the other blood cell types and non-cellular components may be implemented.

For example, as suitable method, one may cite physical separation methods, such as centrifugations methods, are suitable. As example of suitable centrifugations methods one may cite gradient density, for example using ficoll.

Also one may use immunological separation methods, such as, for example, magnetic beads and flow cytometry.

In a preferred embodiment, separation of PBMC from the bulk of blood cells and non-cellular components may be done using a centrifugation method, more preferably, a gradient density centrifugation, using ficoll.

Uses and methods in accordance with the invention may be carried out for monitoring an IgE-dependent allergic disease in a previously diagnosed individual. A "previously diagnosed individual" is an individual known for having an IgE-dependent allergy or IgE-dependent allergic disease to a given allergen. Such individual may have been previously diagnosed as having an IgE-dependent allergic disease, for example, either because it has had at least one episode of an IgE-dependent allergic reaction towards a defined allergen, or because it has been subjected to a diagnosing test.

In another embodiment, the invention relates to a method for diagnosing and/or monitoring an IgE-dependent allergic disease to an allergen, in an individual, said method comprising at least the steps of:

(a) contacting for a period of time comprised from about 12 to about 24 h, with an allergen, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

Hence, according to one preferred embodiment, step (a) is performed for a period of from about 12 h to about 24 h, in particular from about 15 h to about 22 h, in particular from about 18 h to about 20 h.

Within the scope of the instant invention, the term "about" means that the specified referred value may vary from minus 10% or plus 10%.

Hence the period in step a) encompasses at least 12 h, at least 13 h, at least 14 h, at least 15 h, at least 16 h, at least 17 h, at least 18 h, at least 19 h, at least 20 h, at least 21 h, at least 22 h, at least 23 h and at most 24 h.

In another preferred embodiment, step (a) is performed for a period strictly inferior to 18 h.

In particular, the period in step a) encompasses at least 12 h, at least 13 h, at least 14 h, at least 15 h, at least 16 h, at least 17 h and is strictly inferior to 18 h.

Without to be bound to a theory, the inventors consider that this period of time for contacting the T cells with an allergen is suitable to favor the detection of memory T cells, whereas naïve T cells would necessitate a much longer contacting period to secrete cytokines, such as at least 24 h.

According to another embodiment, uses and methods according to the invention may, in particular, allow for the identification and evaluation of potential active drugs towards an IgE-dependent allergic disease.

According to one embodiment, uses and methods of the invention may be for assessing a responsiveness of an individual to a drug presumed efficient to an IgE-dependent allergic disease.

According to another embodiment, uses and methods of the invention may be for assessing an effectiveness of a drug presumed efficient against an IgE-dependent allergic disease.

According to another embodiment, uses and methods of the invention may be for assessing a therapeutic efficacy of a drug as a therapeutic agent for preventing and/or treating an IgE-dependent allergic disease into an individual suffering or presumed suffering from said allergic disease.

The number of IL-4 and/or IL-13 secreting T-cells may be used to monitor or manage an individual's treatment of an IgE-dependent allergic disease.

A method of assessing or monitoring an efficacy of a drug presumed efficient in an individual may involve measuring a number of IL-4 and/or IL-13 secreting T-cells in a biological sample isolated from said individual after administration of said drug, and comparing the measured number to a number of IL-4 and/or IL-13 secreting T-cells measured in biological sample isolated from said individual before administration of said drug. By following the number of IL-4 and/or IL-13 secreting T-cells, the activity, or efficiency, of the drug may be monitored over time.

According to one embodiment, uses or methods according to the invention may be implemented for optimizing a dosing regimen of an individual administered with a treatment against an IgE-dependent allergic disease. Individuals suffering from a given IgE-dependent allergic disease may respond differently to a given drug presumed efficient against said IgE-dependent allergic disease, depending on factors such as age, health, genetic background, presence of other complications, disease progression, and the co-administration of other drugs. It may be useful to utilize the number of IL-4 and/or IL-13 secreting T-cells biomarker to assess and optimize the dosage regimen, such as the dose amount and/or the dose schedule, of a drug presumed efficient against an IgE-dependent allergic disease in an individual. In this regard the number of IL-4 and/or IL-13 secreting T-cells can also be used to track and adjust individual treatment effectiveness over time. The number of IL-4 and/or IL-13 secreting T-cells can be used to gather information needed to make adjustments in an individual's treatment, increasing or decreasing the dose of drug as needed. For example, an individual receiving a drug presumed efficient against an IgE-dependent allergic disease can be tested using the number of IL-4 and/or IL-13 secreting T-cells to see if the dosage is becoming effective, or if a more aggressive treatment plan needs to be put into place. The amount of administered drug, the timing of administration, the administration frequency, the duration of the administration may be then adjusted depending on the number of IL-4 and/or IL-13 secreting T-cells measurement.

The number of IL-4 and/or IL-13 secreting T-cells may also be used to track individual compliance during treatment regimes, or during clinical trials. This can be followed at set intervals to ensure that the individuals included in the trial are taking the drugs as instructed. Furthermore, an individual receiving a drug presumed efficient against an IgE-dependent allergic disease can be tested using the number of IL-4 and/or IL-13 secreting T-cells to determine whether the individual complies with the dosing regimen of the treatment plan. A decreased number of IL-4 and/or IL-13 secreting T-cells compared to that of an untreated control sample is indicative of compliance with the protocol.

According to another embodiment of the invention, when monitoring an IgE-dependent allergic disease or an efficacy of an IgE-dependent allergic disease treatment, an individual may be tested with a method or a use of the invention at a time interval selected from the group consisting of hourly, twice a day, daily, twice a week, weekly, twice a month, monthly, twice a year, yearly, and every other year. The then collected isolated biological samples can be tested immediately, or can be stored for later testing.

A method for screening a drug presumed effective in preventing and/or treating an IgE-dependent allergic disease in accordance with the invention may comprise at least the steps of:

(a) treating at least one population of T-cells able to secrete IL-4 and/or IL-13 with said drug, said population of T-cells being contacted with an allergen inducing a secretion of IL-4 and/or IL-13, (b) measuring a number of IL-4 and/or IL-13 secreting T-cells in said treated population of T-cells, (c) comparing said measured number of IL-4 and/or IL-13 secreting T-cells with a number of IL-4 and/or IL-13 secreting T-cells from at least one population of T-cells contacted with an allergen inducing a secretion of IL-4 and/or IL-13 and non-treated with said drug.

A decreased measured number of IL-4 and/or IL-13 secreting T-cells may indicative of an efficacy of said drug against said IgE-dependent allergic disease.

According to one embodiment, the number of IL-4 and/or IL-13 secreting T-cells is compared with a reference value.

A reference value may be a negative or a positive reference value. A negative reference value is a reference value obtained in absence of molecule liable to induce secretion of IL-4 and/or IL-13 by T-cells. For example, a negative reference value may be obtained in presence of a buffer. A positive reference value is a reference value obtained in presence of a molecule liable to induce secretion of IL-4 and/or IL-13 by T-cells. For example, a positive reference value may be obtained in presence of phyto-hemagglutinin (PHA).

According to one embodiment, when diagnosing or monitoring an IgE-dependent allergic disease, an increase of the measured number of IL-4 and/or IL-13 secreting T-cells relative to a negative reference value may be indicative of an IgE-dependent allergic disease, and preferably may be indicative of an IgE-dependent allergic disease to an assayed allergen. Also, an observation of an increase of a number of IL-4 and/or IL-13 secreting T-cells as compared to a negative reference value may be indicative of the severity of an IgE-dependent allergic disease. An observation of a decrease of a number of IL-4 and/or IL-13 secreting T-cells as compared to a positive reference value may be indicative of a decrease of the severity of an IgE-dependent allergic disease.

According to another embodiment, when screening or essaying a drug efficacy against an IgE-dependent allergic disease, a decrease of the measured number of IL-4 and/or IL-13 secreting T-cells relative to a positive reference value may be indicative of an efficacy of an assayed or administered drug presumed efficient or active against an IgE-dependent allergic disease.

Reference value to be used for comparing the number of IL-4 and/or IL-13 secreting T-cells in a tested isolated biological sample may be obtained from a control isolated biological sample.

Control samples can be taken from various sources. In some embodiments, control samples are taken from the individual prior to treatment or prior to the presence of the disease (such as an archival blood sample). In other embodiments, the control samples are taken from a set of normal, non-diseased members of a population. In another embodiment, a cell assay can utilize a control cell culture, for example, that has not been treated with a tested drug or has been treated with a reference drug.

According to one embodiment, for the diagnosing of or monitoring an IgE-dependent allergic disease in an individual, a negative reference value may be obtained from an isolated biological sample obtained from an individual or a group of individuals known to not suffer from such disease.

According to one embodiment, for the diagnosing of or monitoring an IgE-dependent allergic disease in an individual, a positive reference value may be obtained from an isolated biological sample obtained from an individual or a group of individuals known to suffer from such disease, and treated with an allergen able to elicit said disease.

According to another embodiment, for the screening of or monitoring an efficacy of a treatment of an IgE-dependent allergic disease into an individual, a negative reference value may be obtained from an isolated biological sample obtained from an individual or a group of individuals known to not suffer from such disease, and not receiving the treatment the efficacy of which is to be determined or monitored. Alternatively, a negative reference value may be obtained from an isolated biological sample obtained from an individual suffering from an IgE-dependent allergic disease and receiving a treatment the efficacy of which being to be determined or monitored, the isolated biological sample being taken from the individual before administration of the treatment, and being not contacted with an allergen able to elicit said disease.

According to another embodiment, for the screening or monitoring of an efficacy of a treatment of an IgE-dependent allergic disease into an individual, a positive reference value may be obtained from an isolated biological sample obtained from an individual or a group of individuals known to suffer from such disease, contacted with an allergen able to elicit said disease, and not treated with the treatment the efficacy of which is to be determined or monitored. Alternatively, a positive reference value may be obtained from an isolated biological sample obtained from an individual suffering from an IgE-dependent allergic disease and receiving a treatment the efficacy of which being to be determined or monitored, the isolated biological sample being taken from the individual before administration of the treatment, and being contacted with an allergen able to elicit said disease.

Preferably, a number of IL-4 and/or IL-13 secreting T-cells is a mean number obtained from repeated measures. Repeated measures may be obtained preferably from replicate, i.e. different measures on a same sample.

In methods of the invention for diagnosing or monitoring an IgE-dependent allergic disease, one may carry out a step of observing a deviation between a number of IL-4 and/or IL-13 secreting T-cells measure in a biological sample from a reference value.

An observed deviation, and in particular an observed increase of a number of IL-4 and/or IL-13 secreting T-cells from a negative reference value, may be indicative of an IgE-dependent allergic disease, and in particular of the severity of an IgE-dependent allergic disease.

An observed deviation, and in particular an observed decrease of a number of IL-4 and/or IL-13 secreting T-cells from a positive reference value, may be indicative of a relieving of an IgE-dependent allergic disease or of an efficacy of a therapeutic treatment or a screened drug.

The intensity of the observed decrease or increase may be correlated to the intensity of the manifestation of, and in particular to the symptoms associated with, an IgE-dependent allergic disease.

An increase of a number of IL-4 and/or IL-13 secreting T-cells may be at least about two-fold, for example of about three-fold, for example of about four-fold, for example of about six-fold, for example of about eight-fold, or for example of about ten-fold increase relative to said reference value.

An decrease of a number of IL-4 and/or IL-13 secreting T-cells may be at least about two-fold, for example of about three-fold, for example of about four-fold, for example of about six-fold, for example of about eight-fold, or for example of about ten-fold decrease relative said reference value.

A reference value may be obtained at the same time as the measured number of IL-4 and/or IL-13 secreting T-cells obtained from the individual to be tested, or at a different time, or even different times.

According to another embodiment, the invention relates to a method to monitor desensitization to an allergen able to elicit an IgE-dependent allergic disease in an individual in need thereof.

For the scope of the instant invention, "desensitization" means restoring immune tolerance to an allergen able to elicit an IgE-dependent allergic disease.

According to one embodiment, the treatment of an IgE-dependent allergic disease and/or a desensitization treatment is immunotherapy.

The invention relies upon a measure of a number of IL-4 and/or IL-13 secreting T-cells, which may carried out by any suitable technique known in the art.

A measure of a number of IL-4 and/or IL-13 secreting T-cells may be carried out by ELISpot (Enzyme-Linked Immunosorbent Spot).

An ELISpot assay allows the identification and enumeration of cytokine-producing cells at the single cell level. The ELISpot assay allows visualization of the secretory product of individual activated or responding cells. Each spot that develops in the assay represents a single reactive cell. Thus, the ELISpot assay provides both qualitative (type of immune protein) and quantitative (number of responding cells) information.

Advantageously, an ELISpot assay allows identifying allergen-specific T-cells at a single cell level without long-term in vitro culture. Therefore, the measured response closely mirrors the in vivo cellular frequency in a patient.

Within the invention, an ELISpot may be carried out according to any known proceedings in the art.

According to one embodiment, a first monoclonal or polyclonal capture antibody may be coated onto a polystyrene or PVDF (polyvinylidene fluoride)-backed microplate comprising wells. The first antibodies are chosen for their specificity for the analyte in question. According to the inventive, the first antibodies may be directed to IL-4, IL-13, or IL-4 and IL-13.

The plate may be blocked, usually with a serum protein that is non-reactive with any of the antibodies in the assay. In particular, the plate may be blocked for 1 hour at 37° C. with a blocking solution. After this, cells of interest, and in particular T-cells or PBMCs, may be plated out at varying densities, along with an allergen to be assayed, and then placed in a humidified 37° C. $CO_2$ incubator for a specified period of time. According to one embodiment, the period of time for contacting said T-cells or PBMCs with said allergen may range from 12 to 24 hours, in particular from 18 to 24 hours, in particular from 18 to 20 hours. PBMCs or T-cells may be, for example, advantageously plated at a density of about $0.3 \times 10^6$ cells per well.

In another most preferred embodiment, the instant invention relates to an in vitro method for diagnosing and/or monitoring an IgE-dependent allergic disease to an allergen, in an individual, said method comprising at least the steps of:

(a) contacting for a period of from about 12 h to about 24 h, with an allergen, an isolated biological sample from said individual, said sample comprising memory T-cells, in conditions suitable for said memory T-cells to secrete IL-4 and/or IL-13; and (b) measuring by ELISpot a number of IL-4 and/or IL-13 secreting memory T-cells contained in said biological sample.

In another embodiment, the instant invention relates to an in vitro method for diagnosing and/or monitoring an IgE-dependent allergic disease to an allergen, in an individual, said method comprising at least the steps of:

(a) contacting for a period strictly inferior to 18 h, with an allergen, an isolated biological sample from said individual, said sample comprising memory T-cells, in conditions suitable for said memory T-cells to secrete IL-4 and/or IL-13; and (b) measuring by ELISpot a number of IL-4 and/or IL-13 secreting memory T-cells contained in said biological sample.

The cytokines IL-4 and/or IL-13 secreted by activated T-cells are captured locally by the coated first antibodies on the high surface area PVDF membrane.

After washing the wells to remove cells, debris, and media components, a second antibody specific for the cytokine is added to the wells. This second antibody may be polyclonal or monoclonal and is reactive with a distinct epitope of the cytokine. This second antibody may comprise a marker allowing its detection (detectable marker).

A marker suitable for the invention may be a moiety capable of generating a signal, for example colorimetric, luminescent, in particular fluorescent, or radioactive, or may be a moiety allowing the specific binding of an entity capable of generating a signal, such as a biotin, a streptavidin, or a polyhistidine tag, or may be the Fc portion of the second antibody.

A luminescent marker, and in particular a fluorescent marker, suitable for the invention may be any marker commonly used in the field such as fluorescein, BODIPY, fluorescent probes type ALEXA, coumarin and its derivatives, phycoerythrin and its derivatives, or fluorescent proteins such as GFP or the DsRed.

A radioactive moiety suitable for the invention may for example $^3H$, $^{121}I$, $^{123}I$, $^{99m}Tc$, $^{14}C$ or $^{32}P$.

Antibody bearing a biotin, a streptavidin or a polyhistidine tag may be detected further to a step of contacting the plate with an entity capable of generating a detectable signal and able to bind specifically to the corresponding marker, such as respectively, a streptavidin, a biotin or antibody binding the polyhistidine tag. Such entity may be in particular an enzyme.

In particular, biotinylated-antibodies may be detected further to a step of contacting the plate with an avidin-labeled enzyme. Such an entity allows the generation of colored product following hydrolyzing of a precipitating chromogenic substrate. For example, a labeling enzyme suitable for the invention may be an alkaline phosphatase, a tyrosinase, a peroxydase, or a glucosidase. For example, suitable avidin-labeled enzyme may be an avidin-Horse Radish Peroxydase (HRP), and a suitable substrate may be AEC, 5-bromo-4-chloro-3-indolyl phosphate (BCIP), nitro blue tetrazolium chloride (NBT).

The Fc portion of the second antibody may be detected further to a step of contacting the plate with a secondary antibody labeled with a detectable marker suitable for the invention. Such a secondary antibody may be labeled with a detectable marker as described above. In particular, a secondary antibody may be labeled with a biotin or an enzyme as above-described.

A secondary antibody suitable for the invention may be a GABA (phi-labeled anti-biotin antibodies), for example commercialized by U-Cytech In a preferred embodiment, the IL-4 and/or IL-13 bound to the first antibodies coated into the wells may be detected and visualized by means of second antibodies subsequently bound to labeled secondary antibodies.

Following a wash to remove any unbound second antibody, the detected cytokine is then visualized with means adapted to the second antibody and its marker.

Means of detection of the bound cytokines will be naturally adapted to the detectable marker implemented and to the measure of a number of IL-4 and/or IL-13 secreting T-cells.

Thus, means of detection for the invention may be, for example, a colorimetric detection system, a fluorescence or UV-visible spectroscopy system, or a detection system for radioactivity.

According to one embodiment, means of detection especially considered by the invention are based on a colorimetric detection system visible, especially with the naked eye.

The colored end product (a spot) typically represents an individual cytokine-producing T-cell. The spots can be counted manually (e.g., with a dissecting microscope) or using an automated reader to capture the microwell images and to analyze spot number and size. The number of the spots gives the number of IL-4 and/or IL-13 secreting T-cells.

Suitable antibodies for the invention may be a polyclonal or monoclonal type IgG, IgA, IgM, or IgE. An antibody suitable for the invention may be selected from antibodies from mouse, rat, rabbit, goat, horse, llama, human or other primate.

An antibody fragment having binding properties defined above may also be suitable for the invention. By "antibody fragment" is meant a portion of an antibody such as Fab, Fab', F(ab)2, F(ab')2 fragments and other similar. These terms also include any synthetic or genetically engineered protein that can act as an antibody by binding to a detectable protein of the invention, in a protein complex as defined above.

An antibody or antibody fragment suitable for the invention may be prepared by any method known to those skilled in the art, as described, for example, in "Making and using antibodies: a practical handbook" (Howard & Kaser, Ed CRC, 2006).

IgE-Dependent Allergic Disease

As stated above, an IgE-dependent allergic disease considered within the invention may be selected from the group consisting of airborne allergies, food allergies and insect allergies.

According to a particular embodiment, an allergic disease considered within the invention may be an airborne allergy or a food allergy.

Further to an hypersensitivity of the immune system to normally harmless substances or molecules of the environment, an allergy disease may be qualified by means of different symptoms among which are sneezing, rhinitis, asthma, conjunctivitis, sinusitis, dry eye, hitching, rash, redness, blistering, weeping, hives, angioedema (swelling), atopic dermatitis, nausea, vomiting, diarrhea, abdominal pain, confusion, dizziness and/or rapid pulse.

IgE-dependent allergic diseases may be triggered by a great diversity of allergens.

For example, among allergens able to elicit an airborne or respiratory allergy, one may cite pollen, grass, mold, house dust mite (HDM), pet saliva, urine and fur. All these allergens are airborne, and can be seasonal or year round sustained in the air.

Any food or food component may comprise a food allergen.

Within the scope of the present invention, allergens able to elicit a food allergy may be selected from the group consisting of peanut; milk; shellfish, in particular such as shrimp, crab, lobster, oyster or scallops; tree nuts, in particular such as pecan, pistachio, pine nut, walnut, hazelnut, cashew, almond; chicken eggs; soy; wheat; maize; fish; fruits; vegetables; seeds, in particular such as sesame, poopy, cotton, mustard; and spices.

Among allergens able to elicit an insect allergy, one may cite venom from stinging insects, in particular such as bees, wasps.

According to a preferred embodiment, an allergen considered within the invention may be an allergen able to elicit an airborne allergy or a food allergy.

According to a more preferred embodiment, an allergen considered within the invention may be an allergen from house dust mite, cow's milk or peanut.

Kit

A kit of the invention comprises:

(a) at least a composition comprising antibodies directed against IL-4 and/or IL-13;

(b) at least a compound known to stimulate IL-4 and/or IL-13 T cells secretion; and (c) at least a mean for detecting IL-4 and/or IL-13 antibodies.

According to one embodiment, a composition comprising antibodies against IL-4 and/or IL-13 suitable for a kit of the invention may comprise the first antibodies as previously described.

According to one embodiment, a compound known to stimulate IL-4 and/or IL-13 T cells secretion may be phytohemagglutinin A. Such compound may be used to obtain a positive reference value.

According to one embodiment, a mean for detecting IL-4 and/or IL-13 antibodies may be a second antibody comprising a detectable marker as above described.

According to the detectable marker used, a kit of the invention may further comprise an entity capable of generating a signal and able to bind specifically to the corresponding marker as above described or a secondary antibody labeled with a detectable marker as above described. Accordingly, a kit of the invention may further comprise a precipitating chromogenic substrate.

According to another embodiment, a kit of the invention may comprise at least (d) a device comprising a support and configured to receive a biological sample to be tested.

A device suitable for the invention may be, for example a polystyrene or PVDF (polyvinylidene fluoride)-backed microplate comprising wells, and in particular a 96-well microplate.

Also a device suitable for the invention may be a lab-on-chip or a micro-chip, as known in the art.

According to another embodiment, a kit of the invention may further comprise at least one allergen to be assayed, which allergen is able to elicit an IgE-dependent reaction. An allergen to be assayed may, for example be chosen among the allergens above-indicated.

According to another embodiment, a kit of the invention may further comprise at least secondary antibodies able to specifically bind an IL-4 or an IL-13 antibodies, and bearing an entity able to generate detectable signal as above described. In particular, such entity may an enzyme as above-described. In such embodiment, a kit of the invention may further comprise a precipitating chromogenic substrate.

Cow's Milk Allergy

Cow's milk allergy (CMA) is the most common food allergy in children, with rates estimated at 2% to 3%. Between 19% and 78% of subjects outgrow their milk allergy by 5 years of age depending on publications. Furthermore, over the past two decades, the incidence of food allergies, and more particularly cow's milk allergy, has increased, especially in children with a delay of spontaneous regression during childhood.

CMA, and food allergies in general, can induce from mild itching to life-threatening anaphylaxis.

There is currently no biomarker able to reliably confirm with good specificity and sensitivity the presence or absence of CMA or to predict remission or support that tolerance was induced in an individual.

Larger skin prick test weal size has been associated with persistence of CMA. Low levels of cow's milk proteins specific IgE were associated with recovery whereas levels higher than 50 kU/L were associated with the persistence of allergy. Casein specific IgE monitoring was described to have the best specificity to predict CMA.

In such context, oral food challenge (provocation test) is still the gold standard test to assess the presence or absence of CMA according to international guidelines. However, this test is expensive, laborious, requiring a specialized environment and potentially associated with a risk for anaphylaxis and even death. Therefore, it is highly relevant to develop a biological test that may confirm or refute the diagnosis of food allergy as well as determine thresholds reactivity to the oral food challenge. The present invention relates to an in vitro use of a number of IL-4 and/or IL-13 secreting T-cells as a biomarker for diagnosing and/or monitoring a cow's milk allergy.

In another embodiment, the instant invention relates to an in vitro use of a number of IL-4 and/or IL-13 secreting T-cells as a biomarker for screening or assessing an activity of a drug presumed effective in preventing and/or treating a cow's milk allergy.

In another embodiment, the invention relates to an in vitro method for diagnosing a cow's milk allergy, in an individual, said method comprising at least the steps of:

(a) contacting, with cow's milk, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

In another embodiment, the instant invention relates to an in vitro method for monitoring a cow's milk allergy, in a previously diagnosed individual, said method comprising at least the steps of:

(a) contacting, with cow's milk, an isolated biological sample from said individual, said sample comprising T-cells, in conditions suitable for said T-cells to secrete IL-4 and/or IL-13; and (b) measuring a number of IL-4 and/or IL-13 secreting T-cells.

In one embodiment, the instant invention relates to an in vitro method for diagnosing and/or monitoring a cow's milk allergy, in an individual, said method comprising at least the steps of:

(a) contacting for a period of from about 12 h to about 24 h, with cow's milk, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

In another embodiment, the instant invention relates to an in vitro method for diagnosing and/or monitoring a cow's milk allergy, in an individual, said method comprising at least the steps of:

(a) contacting for a period strictly inferior to 18 h, with cow's milk, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

In another most preferred embodiment, the instant invention relates to an in vitro method for diagnosing and/or monitoring a cow's milk allergy, in an individual, said method comprising at least the steps of:

(a) contacting for a period of from about 12 h to about 24 h, with an allergen, an isolated biological sample from said individual, said sample comprising memory T-cells, in conditions suitable for said memory T-cells to secrete IL-4 and/or IL-13; and (b) measuring by ELISpot a number of IL-4 and/or IL-13 secreting memory T-cells contained in said biological sample.

In another preferred embodiment, the instant invention relates to an in vitro method for diagnosing and/or monitoring a cow's milk allergy, in an individual, said method comprising at least the steps of:

(a) contacting for a period strictly inferior to 18 h, with an allergen, an isolated biological sample from said individual, said sample comprising memory T-cells, in conditions suitable for said memory T-cells to secrete IL-4 and/or IL-13; and (b) measuring by ELISpot a number of IL-4 and/or IL-13 secreting memory T-cells contained in said biological sample.

In a still further embodiment, the present invention relates to an in vitro method for screening a drug presumed effective in preventing and/or treating a cow's milk allergy, comprising at least the steps of:

(a) treating at least one population of T-cells able to secrete IL-4 and/or IL-13 with said drug, said population of T-cells being contacted with cow's milk inducing a secretion of IL-4 and/or IL-13, (b) measuring a number of IL-4 and/or IL-13 secreting T-cells in said treated population of T-cells.

In one preferred embodiment, the invention relates to a method further comprising a step of comparing said measured number of T cells with a reference value.

In another embodiment, the invention relates to an in vitro method for assessing an activity of drug presumed efficient for preventing and/or treating a cow's milk allergy in an individual treated with said drug, comprising at least the steps of:

(a) measuring a number of IL-4 and/or IL-13 secreting T-cells, in a first isolated biological sample from said individual before a treatment with said drug and in a second isolated biological sample from said individual after a treatment with said drug; and (b) determining if said number of IL-4 and/or IL-13 secreting T-cells is decreased in the first biological sample obtained after the treatment as compared to the second biological sample obtained before the treatment;

wherein a decreased number of IL-4 and/or IL-13 secreting T-cells in the second sample relative to the first sample is indicative of an activity of said drug.

In another embodiment, the invention relates to a method to monitor desensitization to cow's milk able to elicit a cow's milk allergy in an individual in need thereof, comprising measuring a number of IL-4 and/or IL-13 secreting T-cells in a biological sample isolated from said individual after administration of a desensitization treatment, and comparing the measured number to a number of IL-4 and/or IL-13 secreting T-cells measured in biological sample isolated from said individual before administration of the desensitization treatment.

In a still preferred embodiment, the invention relates to any above method wherein a number of T-cells secreting IL-4 and a number of T-cells secreting IL-13 are measured.

In another still preferred embodiment, the invention relates to any above method wherein said measuring of the number of IL-4 and/or IL-13 secreting T cells is carried out by ELISpot.

In another embodiment, the instant invention relates to a kit for diagnosing and/or monitoring a cow's milk allergy, said kit comprising:

(a) at least a composition comprising antibodies directed against IL-4 and/or IL-13;

(b) at least a compound known to stimulate IL-4 and/or IL-13 T cells secretion; and (c) at least a mean for detecting IL-4 and/or IL-13 antibodies.

In a still preferred embodiment, the present invention relates to a kit for diagnosing and/or monitoring a cow's milk allergy further comprising at least (d) a device comprising a support and configured to receive a biological sample to be tested.

In a still preferred embodiment, the invention relates to a kit for diagnosing and/or monitoring a cow's milk allergy further comprising at least one cow's milk extract.

House Dust Mite Allergy

House dust mite (HDM) is the most common per annual allergen and is responsible for symptomatic allergy manifestations ranging from allergic rhinitis to severe asthma. Allergen immunotherapy is the only specific treatment which cures the underlying allergic disorder. Treating allergy, it also allows the improvement of a pre-existant asthma and prevents the development of new sensitizations. Allergic polysensitization is a frequent phenotype of allergic asthma. Hence, the importance of defining exactly the major allergen responsible of allergic symptoms before starting specific immunotherapy is essential.

Currently, the bronchial provocation test and nasal provocation test are the gold standards for diagnosis of mite allergy. These are invasive tests, presenting well known risks, currently mainly used in clinical research.

In vitro immunological tests routinely used are the determination of specific immunoglobulin E (IgE) that is indicative of the sensitization to the allergen but not the allergy itself. The only functional test currently used is the basophil activation test. This test recently developed still has not been proven superior in the diagnosis of mite allergy compared to the dosage of specific IgE.

The present invention relates to an in vitro use of a number of IL-4 and/or IL-13 secreting T-cells as a biomarker for diagnosing and/or monitoring a house dust mite allergy.

In another embodiment, the instant invention relates to an in vitro use of a number of IL-4 and/or IL-13 secreting T-cells as a biomarker for screening or assessing an activity of a drug presumed effective in preventing and/or treating a house dust mite allergy.

In another embodiment, the invention relates to an in vitro method for diagnosing a house dust mite allergy, in an individual, said method comprising at least the steps of:

(a) contacting, with house dust mite extract, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

In another embodiment, the instant invention relates to an in vitro method for monitoring a house dust mite allergy, in a previously diagnosed individual, said method comprising at least the steps of:

(a) contacting, with house dust mite extract, an isolated biological sample from said individual, said sample comprising T-cells, in conditions suitable for said T-cells to secrete IL-4 and/or IL-13; and (b) measuring a number of IL-4 and/or IL-13 secreting T-cells.

In another preferred embodiment, the invention relates to an in vitro method for diagnosing and/or monitoring a house dust mite allergy, in an individual, said method comprising at least the steps of:

(a) contacting for a period of from about 12 h to about 24 h, with house dust mite extract, an isolated biological sample from said individual, said sample comprising T-cells, in conditions suitable for said T-cells to secrete IL-4 and/or IL-13; and (b) measuring a number of IL-4 and/or IL-13 secreting T-cells contained in said biological sample.

In another most preferred embodiment, the invention relates to an in vitro method for diagnosing and/or monitoring a house dust mite allergy, in an individual, said method comprising at least the steps of:

(a) contacting for a period of from about 12 h to about 24 h, with house dust mite extract, an isolated biological sample from said individual, said sample comprising memory T-cells, in conditions suitable for said memory T-cells to secrete IL-4 and/or IL-13; and (b) measuring by ELISpot a number of IL-4 and/or IL-13 secreting memory T-cells contained in said biological sample.

In another embodiment, step a) is performed for a period strictly inferior to 18 h.

In a still further embodiment, the present invention relates to an in vitro method for screening a drug presumed effective in preventing and/or treating a house dust mite allergy, comprising at least the steps of:

(a) treating at least one population of T-cells able to secrete IL-4 and/or IL-13 with said drug, said population of T-cells being contacted with house dust mite extract inducing a secretion of IL-4 and/or IL-13, (b) measuring a number of IL-4 and/or IL-13 secreting T-cells in said treated population of T-cells.

In one preferred embodiment, the invention relates to a method further comprising a step of comparing said measured number of T cells with a reference value.

In another embodiment, the invention relates to an in vitro method for assessing an activity of drug presumed efficient for preventing and/or treating a house dust mite allergy in an individual treated with said drug, comprising at least the steps of:

(a) measuring a number of IL-4 and/or IL-13 secreting T-cells, in a first isolated biological sample from said individual before a treatment with said drug and in a second isolated biological sample from said individual after a treatment with said drug; and (b) determining if said number of IL-4 and/or IL-13 secreting T-cells is decreased in the first biological sample obtained after the treatment as compared to the second biological sample obtained before the treatment;

wherein a decreased number of IL-4 and/or IL-13 secreting T-cells in the second sample relative to the first sample is indicative of an activity of said drug.

In another embodiment, the invention relates to a method to monitor desensitization to house dust mite able to elicit a house dust mite allergy in an individual in need thereof, comprising measuring a number of IL-4 and/or IL-13 secreting T-cells in a biological sample isolated from said individual after administration of a desensitization treatment, and comparing the measured number to a number of IL-4 and/or IL-13 secreting T-cells measured in biological sample isolated from said individual before administration of the desensitization treatment.

In a still preferred embodiment, the invention relates to any above method wherein a number of T-cells secreting IL-4 and a number of T-cells secreting IL-13 are measured.

In another still preferred embodiment, the invention relates to any above method wherein said measuring of the number of IL-4 and/or IL-13 secreting T cells is carried out by ELISpot.

In another embodiment, the instant invention relates to a kit for diagnosing and/or monitoring a house dust mite allergy, said kit comprising:

(a) at least a composition comprising antibodies directed against IL-4 and/or IL-13;

(b) at least a compound known to stimulate IL-4 and/or IL-13 T cells secretion; and (c) at least a mean for detecting IL-4 and/or IL-13 antibodies.

In a still preferred embodiment, the present invention relates to a kit for diagnosing and/or monitoring a house dust mite allergy further comprising at least (d) a device comprising a support and configured to receive a biological sample to be tested.

In a still preferred embodiment, the invention relates to a kit for diagnosing and/or monitoring a house dust mite allergy further comprising at least one house dust mite extract.

The examples presented hereafter are for illustrating purpose of the invention and should not be construed as limiting the scope of the invention.

EXAMPLES

Example 1

The Number of IL-4 and IL-13 Secreting House Dust Mite (HDM) Specific T-Cells is Correlated with Allergic Disease and with Seasonal Variations 1—Materials and Methods a—Study Design This was a cross sectional study performed in consecutive asthmatic patients before undergoing specific immunotherapy to HDM. Patients were part of the 2 years (2011-2012) Trousseau Asthma Program of the "Centre de l'Asthme et des Allergies" at the Hôpital Trousseau in Paris. The study protocol was approved by the Paris 5 ethics committee and all patients gave written informed consent.

b—Patient Population

Inclusion criteria for the study were: 1) age higher than 5 years, 2) diagnosis of active asthma (defined as a history of recurrent wheeze or more than 3 episodes of reversible bronchial obstruction documented within the previous 6 months), 3) absence of other chronic obstructive pulmonary diseases (congenital or acquired), 4) presence of allergic sensitization to HDM defined as positive skin prick test (wheal≥3 mm compared to negative control and specific IgE≥0.35 kU/L against *Dermatophagoides pteronyssinus*) in absence of sensitization to per annual allergens (mould, cockroach, cat and dog) and of clinical symptoms of seasonal allergy (birch and grass pollen), 5) the achievement of clinical examination outside of episodes of exacerbation or acute respiratory illness before initiation of specific immunotherapy and finally 6) having no previous specific immunotherapy.

Asthma was defined as intermittent, mild persistent, moderate persistent or severe persistent according to the Global Initiative for Asthma (GINA) 2005. All enrolled children were treated with fixed doses of inhaled corticosteroids (ICS) for at least 6 months and were compliant with their prescribed treatment. High doses of ICS were defined as 500 µg or more of fluticasone (or its equivalent) per day. The control of asthma was assessed according to GINA 2009 and to Asthma Control Test (ACT). The outcome of treatment was ranked as: controlled with or without high-dose of inhaled corticosteroids (ICS), or uncontrolled (including partially controlled) with or without high-dose of ICS.

Allergic rhinitis, was assessed using the questionnaire from the International Study of Asthma and Allergies in Childhood (ISAAC) and rhinitis severity was determined according to the World Health Organization (WHO) Allergic Rhinitis and its Impact on Asthma (ARIA) Guidelines, based on the impact of rhinitis upon patient quality of life.

c—Biological Markers

Serum levels of total immunoglobulin E (IgE) and specific antibodies (IgE, IgG4) against *Dermatophagoides pteronyssinus* were determined in whole blood using the immunoCAP-System (Thermo Fischer, Uppsala, Sweden).

d—ELISpot Assay

Blood samples were collected before starting desensitization in citrate phosphate dextrose adenine (CPDA)-pretreated blood collection tubes. They were stored at room temperature and processed within 24 hours following collection.

Mononuclear cells were isolated by density gradient centrifugation.

Ninety-six well PVDF (Millipore) plates were permeabilized for 1 minute using 35% ethanol, washed five times with PBS and coated overnight at 4° C. with antibodies to IL-4 or IL-13 following the manufacturer's instructions (U-Cytech, Utrecht, The Netherlands).

Then, the plates were incubated for 1 hour at 37° C. with blocking solution (U-Cytech CT360) and washed 3 times with PBS. PBMCs were resuspended in culture medium (RPMI 1640 from Invitrogen containing L-glutamine and supplemented with penicillin, streptomycin and 10% fetal calf serum) and added at $0.3 \times 10^6$ per well in triplicates to coated plates together with HDM extract, from *Dermatophagoides pteronyssinus*, or phyto-hemagglutinin as positive control (PHA, 10 µg/ml, DIFCO) or medium alone as negative control. HDM extract was obtained from Stallergene, France, at a concentration corresponding to 20 µg/ml Derp 1, a major allergen of *Dermatophagoides pteronyssinus*.

After culture for 20-24 hours at 37° C., the cells were removed by extensive washing, and a secondary antibody to IL-4 or IL-13 (U-Cytech) was added and incubated for 1 hour at 37° C. After extensive washing of both sides of the plate, GABA (phi-labeled anti-biotin antibodies) conjugate (U-Cytech) was added for a 1-hour incubation at 37° C. After another series of washings, ActivatorI+II was added to visualize spots. The reaction was stopped 25 minutes later by washing with water and plates were air-dried for 1 hour before spot counting using an ELISpot reader (Autoimmun Diagnostika, Strassberg, Germany).

All data shown are means of triplicate wells and expressed as spot-forming cells per $0.3 \times 10^6$ PBMCs.

The advantage of the ELISpot technique used in the presence, compared to conventional culture (between 5 and 7 days in most cases), is that it is feasible in 24 hours. In addition to the technical ease it offers, it gives a semi-quantitative result of the number of HDM-specific T cells expressing IL-4 and IL-13. Hence, this method gives results that faithfully reflect the in vivo status.

e—Statistical Analysis

Statistical analysis was performed with GraphPad Prism software. Intergroup comparisons of continuous variables were performed with the Mann-Whitney U-test and bivariate correlation was analyzed with the Spearman's rank test. A multiple logistic regression analysis was used to assess the strength and independency of associations, with STATA 12.1 software. Two-sided P-values of <0.05 were considered statistically significant.

2—Results

The study included 26 consecutive children who met the inclusion criteria. 21 were boys (80.8%) and the mean age was 9.14 (±2.85) years (mean±SD). Most of the children had moderate to severe asthma (n=20, 77%). Patients with intermittent to mild persistent rhinitis and patients with moderate to severe persistent rhinitis were evenly distributed (n=13, 50%) (Table 1). Most of them were mono-sensitized to HDM (n=15, 58%).

The number of HDM specific T-cell responses, by ELISpot method, ranged from 0 to 85.2 spots (median 32.15, IQR 11-60.03) for 0.3 million PBMCs for IL-4. It ranged from 0 to 68.7 spots (25.5, 14.78-49.18) for IL-13 (Table 1). As shown in FIG. 1, the two responses were highly correlated (p<0.0001, r=0.88).

The number of IL-4 secreting T-cells in response to HDM significantly varied depending on the season and showed two periods (FIG. 2). An intense response was observed during the fall and early spring compared to a significantly milder response during winter and summer (p=0.002, median difference: 51). The same pattern was observed for the IL-13 responses.

TABLE 1

Subjects characteristics.

| | |
|---|---|
| Number of patients | 26 |
| Gender (male/female) | 21/5 |
| Age (years)[#] | 9.14 +/− 2.85 |
| Intermittent to mild persistent rhinitis[†] | 13 (50%) |
| Moderate to severe rhinitis[†] | 13 (50%) |
| Controlled with low doses ICS[†] | 15 (58%) |
| Uncontrolled with high doses ICS[†] | 4 (15%) |
| Totale IgE (KU/L)*, n = 25 | 294 |
| | (min: 135.5; max: 653.5) |
| HDM specific IgE (KU/L)*, n = 25 | 70 |
| | (min: 28; max: 100) |
| Derp1 specific IgE (KU/L)*, n = 25 | 34.9 |
| | (min: 6.7; max: 84.7) |
| Derp1 specific IgG4 (mgA/L)*, n = 24 | 0.3 |
| | (min: 0.20; max: 0.88) |
| IL-4 secreting T-cells in response to HDM* | 32.15 |
| | (min: 11; max: 60.03) |
| IL-13 secreting T-cells in response to HDM*, n = 24 | 25.5 |
| | (min: 14.78; max: 49.18) |

Values are expressed as median* (interquartile range) or mean[#] (±standard deviation) or number[†] (%).

The results presented here show that the monitoring of specific T-cell response in HDM allergic asthmatic children, and in particular the number of IL-4 or IL-13 secreting T-cells, represents a clinically useful method. In particular, the results show that: first, the number of IL-4 secreting T-cells in response to HDM fluctuates during the year with a peak in autumn and another one in early spring, and secondly, that the number of IL-4 secreting T-cells in response to HDM is significantly correlated to the severity of allergic rhinitis.

Concerning the fact that the number of IL-4 secreting HDM specific T-cells fluctuate with the seasons, with a higher response in the fall and in early spring, it is interesting to note that these two seasonal peaks correspond to wet periods during which HDM allergen exposure is higher. Indeed, mite allergen exposure varies with the seasons with an increase in wet seasons and a decrease in dry seasons.

The advantage of the ELISpot technique used in the present study, compared to conventional culture (between 5 and 7 days in most cases), is that it is feasible in 24 hours. In addition to the technical ease it offers, it gives a semi-quantitative result of the number of mite-specific T cells expressing IL-4 and IL-13.

Example 2

The Number of IL-4 Secreting HDM Specific T-Cells Correlates with the Severity of Allergic Rhinitis This study was performed according to the material and methods as set forth in Example 1.

As shown in FIG. 3, it was found that the number of IL-4 secreting HDM specific T-cells was significantly different between patients: children with moderate to severe persistent rhinitis had a higher number of IL-4 secreting HDM specific T-cells than those with intermittent to mild persistent rhinitis (p=0.04, FIG. 3).

Also, it was observed that the ELISpot results could predict the severity of the rhinitis. Indeed, in a logistic regression model, the severity of the rhinitis was determined by the number of IL-4 secreting HDM specific T-cells (OR: 1.5; 95% IC 1.1-2.1; p=0.04).

Because specific T-cell response varied depending on the season, it has also been assessed the impact of the season on the number of IL-4 secreting HDM specific T-cells. Again, logistic regression analysis showed that the severity of the rhinitis was explained by the ELISpot result, independently of the season (OR: 2; 1.1-3.8; p=0.04).

In contrast, neither asthma control nor HDM sensitization (specific IgE or IgG4, total IgE) was associated with the rhinitis severity (Table 2).

Such differences were not detectable in the IL-13 secreting HDM T-cell responses.

TABLE 2

Determination of suitable biomarkers for monitoring the severity of house dust mite rhinitis allergy by ELISpot.

|  | OR (95% IC) | p |
|---|---|---|
| Total IgE | 1 (0.9-1) | P = 0.2 |
| HDM specific IgE | 1 (0.9-1.3) | P = 0.7 |
| Specific IgE to Derp1 | 0.9 (0.7-1.1) | P = 0.4 |
| Specific IgG4 to Derp1 | 0.001 ($3.7e^{-10}$-2144.5) | P = 0.4 |
| Asthma control | 1.4 (0.7-2.8) | P = 0.3 |
| Number of IL-4 secreting HDM specific T cells | 1.5 (1.1-2.1) | P = 0.04 |

Statistical analyses indicate that the severity of allergic rhinitis can be predicted by the number of IL-4 secreting HDM specific T-cells and that this result is not influenced by the asthma control or the level of HDM specific IgE.

To the knowledge of the inventors, this is the first time that a biological test can predict a clinically symptomatic allergy independently of a biological sensitization. Moreover, this result is also independent of the season. This confirms the specificity of the test: although the number of HDM specific T-cells fluctuates with the season, the severity of the rhinitis is the determining factor in the outcome of the test.

In conclusion, HDM specific T-cell response detection using IL-4 and IL-13 ELISpot assay is an easy and rapid method that could serve in the future to better monitor HDM allergy.

Example 3

Correlation Between a Number of IL-13 Secreting T-Cells Upon Cow's Milk Allergen Stimulation and Amount of Cow's Milk Allergen 1—Materials and Methods
a—Study Design This was a prospective cross sectional study performed in consecutive food allergic patients before undergoing a tolerance induction to cow's milk. The study protocol was approved by the Paris 5 ethics committee and all patients gave written informed consent.

b—Patient Population

Inclusion criteria for the study were: 1) age higher than 2 years; 2) presence of allergic sensitization to cow's milk, defined as positive skin prick test (wheal≥3 mm compared to negative control and specific IgE≥0.35 kU/L against cow's milk) in absence of recent clinical symptoms of anaphylaxis to cow's milk; 3) the achievement of clinical examination before initiation of the oral provocation test; and 4) and finally having no concomitant acute disease or acute symptom of any chronic disease.

c—Biological Markers

Serum levels of specific antibodies (IgE) against cow's milk were determined in whole blood using the immuno-CAP-System (Thermo Fischer, Uppsala, Sweden).

d—ELISpot Assay

The ELISpot assay was performed as described in Example 1, using antibodies to IL-13 following the manufacturer's instructions (U-Cytech, Utrecht, The Netherlands).

The allergen was casein (α+β3+κ) from Sigma Aldrich at a concentration of 100 µg/ml.

All data shown are means of triplicate wells and expressed as spot-forming cells per $0.3 \times 10^6$ PBMCs.

e—Statistical Analysis

Statistical analysis was performed with GraphPad Prism software. Bivariate correlation was analyzed with the Spearman's rank test. Two-sided P-values of <0.05 were considered statistically significant.

2—Results

FIG. 4 shows a correlation between the number of IL-13 secreting T-cells and the amount of cow's milk ingested.

Those data further validate the versatility of the biological test of the invention, and the use of IL-13 secreting T-cells as a biomarker, to clinically predict and monitor an allergic disease to an allergen.

Example 4

Correlation Between a Number of IL-13 Secreting T-Cells Upon an Arachide Stimulation and an Intensity to Allergic Symptoms Upon Oral Test Provocation 1—Materials and Methods
a—Study Design This was a cross sectional study performed in consecutive food allergic patients before undergoing an oral provocation test to peanut. The study protocol was approved by the Paris 5 ethics committee and all patients gave written informed consent.

b—Patient Population

Inclusion criteria for the study were: 1) age higher than 2 years; 2) presence of allergic sensitization to peanut, as defined as positive skin prick test (wheal≥3 mm compared to negative control and specific IgE≥0.35 kU/L against peanut)

in absence of recent clinical symptoms of anaphylaxis to peanut; 3) the achievement of clinical examination before initiation of the oral provocation test; and 4) and finally having no concomitant acute disease or acute symptom of any chronic disease.

c—Biological Markers

Serum levels of specific antibodies (IgE) against peanut were determined in whole blood using the immunoCAP-System (Thermo Fischer, Uppsala, Sweden).

d—ELISpot Assay/Oral Provocation Test

A blood sample was obtained from patients. An ELISpot assay was performed as described in Example 1, using antibodies to IL-13 following the manufacturer's instructions (U-Cytech, Utrecht, The Netherlands).

The allergen was peanut extract at a concentration of 50 μg/ml.

All data shown are means of triplicate wells and expressed as spot-forming cells per $0.3 \times 10^6$ PBMCs.

Patients were afterwards submitted to a standard oral provocation test (Flinterman et al., 2006; Taylor et al., 2004).

e—Statistical Analysis

Statistical analysis was performed with GraphPad Prism software. Intergroup comparisons of continuous variables were performed with the Mann-Whitney U-test. Two-sided P-values of <0.05 were considered statistically significant.

2—Results

FIG. 5 shows a correlation between the number of IL-13 secreting T-cells and the presence or absence of allergic symptoms upon oral provocation test.

Those data further validate the versatility of the biological test of the invention, and the use of IL-13 secreting T-cells as a biomarker, to clinically predict and monitor an allergic disease to an allergen.

Example 5

Use of Casein-Specific IL-13 and IL-4 Secreting T-Cells Numbers as a Reliable Tool for Diagnosis of Cow's Milk Allergy 1—Materials and Methods a—Study Design A prospective study in children referred with cow's milk allergy has been performed in the Allergology department at the Trousseau Hospital in Paris. The study protocol was approved by the Ile de France V. ethics committee. A written and standardized informed consent was obtained from all parents.

Twenty nine patients were included, mean age was 5±2.1 years (2.8-10.5 yrs) and 62% were boys. Mean age at diagnosis of cow's milk allergy was 4.5 (±3.9) months. Seventeen (59%) reacted to the double blind placebo control oral food challenges and were considered as CMA children.

b—Inclusion Criteria

Children were chosen after diagnosis of IgE mediated cow's milk allergy, as defined by a history of reaction to the ingestion of cow's milk product and positive skin prick test (wheal≥3 mm in the absence of a positive reaction to the negative control) to cow's milk and specific IgE>0.35 kU/L. Children were aged more than age of natural healing, i.e. more than 3 years of age.

c—Double Blind Placebo Control Oral Food Challenge

Double blind placebo control oral food challenges were performed outside of episodes of exacerbation of acute illness. Children were admitted to the allergy clinic on 2 separate days and food challenges were performed under the supervision of an experimented allergist.

Increasing doses of cow's milk were administered 20 minutes apart. Doses were 1, 2, 5, 10, 20, 40 and 80 mL for a cumulative dose of 158 mL, corresponding to 5.7 g of cow's milk proteins. The vehicle used was mashed potatoes with cow's milk or with water for placebo. Challenge was stopped in case of clinical reaction compatible with anaphylaxis. Antihistamine, methylprednisolone, bronchodilator or epinephrine was administered if necessary. Cumulative dose of cow's milk defines the reactive threshold in cow's milk allergic (CMA) children. No clinical reaction to a cumulative dose of 158 mL of cow's milk defined non-allergic (non-CMA).

d—Biological Markers

Measurement of Immunoglobulin E (IgE) and IgG

Serum levels of total IgE and specific IgE and IgG4 against major cow's milk allergen (casein, α-lactalbumin and β-lactoglobulin) were determined in whole blood using the immunoCAP-system (Thermo Fischer, Uppsala, Sweden).

ELISpot Assay to Cow's Milk Protein

ELISpot assay was conducted as in example 3.

e—Statistical Analysis

Data are expressed as means and standard deviation (SD). Quantitative data (immunologic parameters) were compared according to two groups (positive versus negative to test results/<158 vs. >158 mL of milk cumulated dose tolerated) using Mann-Whitney U tests for continuous skewed data and using Fisher's Exact tests for categorical data.

To identify whether monotonic relationships exists between the immunologic parameters and the cumulated dose tolerated, Spearman rank correlation coefficients were calculated. Univariate linear model was fitted to examine the associations between the cumulated dose tolerated and each immunologic parameter. Regression coefficients and confidence intervals provided by the regression models allowed estimating the changes in cumulated dose tolerated quantity (mL) for an increase of 1 (UNIT) in each immunologic parameter.

Sensitivity (Se), specificity (Sp), positive predictive value (PPV) and negative predictive value (NPV) were calculated. The cut-off levels of specific parameters were determined by analysis with the receiver-operating characteristic (ROC) curve. ROC curves were plotted and the area under the curve (AUC) was calculated to quantify the accuracy of the number of casein-specific IL-13 secreting T-cells, casein-specific IL-4 secreting T-cells as well as the ratio casein specific IgE/IgG4, each biomarkers alone or together.

Graphic display and statistical were performed using SAS statistical software version 9.2 (SAS Institute Inc, Cary, N.C.). P-values<0.05 were considered statistically significant for all analyses.

2—Results a—Individuals Statistics

Among the 29 patients included in the protocol 24 blood samples were collected. In every patients, response to phytohemagglutinin (positive control) was over 300 antigen specific T-cells.

Six patients showed a non-specific response with a number of non-specific IL-13 or IL-4 secreting T-cells over 10 and they were excluded from the analysis.

Mean number of casein-specific IL-4 secreting T-cells in response to casein was 24.33 (±17.86) in CMA children and 1.81 (±3.57) in non-CMA children (see Table 3 below).

Mean number of casein-specific IL-13 secreting T-cells was 29.75 (±31.68) in CMA children and 2.42 (±4.17) in non-CMA children (see Table 3 below).

The numbers of circulating IL-4 and IL-13 secreting T-cells in response to cow's milk proteins (casein, α-lactalbumin or β-lactoglobulin) are described in Table 3.

Mean casein-specific IgE was 37.91 kU/L and 8.29 kU/L in the CMA and non-CMA children groups respectively (p=0.006, see Table 3).

TABLE 3

Patients characteristics.

|  | CMA | | Non-CMA | | p-value ($\chi^2$) | Entire population | |
| --- | --- | --- | --- | --- | --- | --- | --- |
|  | n | Mean (SD) | n | Mean (SD) |  | n | Mean (SD) |
| Age (years) | 17 | 5.3 (2.3) | 12 | 4.4 (1.8) | 0.22 | 29 | 5.08 |
| male/female | 11/6 |  | 7/5 |  | 0.95 | 18/11 |  |
| Age at diagnosis (months) | 17 | 3.8 (3.2) | 12 | 5.6 (4.6) | 0.98 | 29 | 4.55 (3.88) |
| Casein sIgE | 12 | 37.9 (75.1) | 15 | 8.29 (18.9) | 0.006 | 27 | 24.7 (58.4) |
| Casein sIgE/IgE | 13 | 0.09 (0.12) | 11 | 0.004 (0.005) | 0.02 | 24 | 0.05 (0.1) |
| ALA sIgE/IgE | 13 | 0.04 (0.04) | 11 | 0.007 (0.01) | 0.008 | 24 | 0.02 (0.04) |
| BLG sIgE/IgE | 13 | 0.02 (0.03) | 11 | 0.01 (0.03) | 0.06 | 24 | 0.02 (0.03) |
| Casein sIgE/sIgG4 | 12 | 0.12 (0.36) | 10 | 0.003 (0.004) | 0.001 | 22 | 0.07 (0.3) |
| ALA sIgE/sIgG4 | 11 | 0.13 (0.33) | 8 | 0.003 (0.006) | 0.001 | 19 | 0.08 (0.3) |
| BLG sIgE/sIgG4 | 9 | 0.015 (0.018) | 10 | 0.006 (0.01) | 0.05 | 19 | 0.01 (0.02) |
| Casein IL-4 T-cells | 6 | 24.33 (17.86) | 8 | 1.81 (3.57) | 0.009 | 14 | 11.46 (16.2) |
| ALA IL-4 T-cells | 6 | 2.58 (3.07) | 8 | 1.88 (4.91) | 0.37 | 14 | 2.18 (4.1) |
| BLG IL-4 T-cells | 6 | 3.08 (4.78) | 8 | 0.88 (2.48) | 0.28 | 14 | 1.8 (3.7) |
| Casein IL-13 T-cells | 12 | 25.46 (31.68) | 9 | 2.42 (4.17) | 0.004 | 21 | 15.6 (26.4) |
| ALA IL-13 T-cells | 9 | 17.56 (28.05) | 8 | 8.85 (11.52) | 0.28 | 17 | 13.5 (21.7) |
| BLG IL-13 T-cells | 9 | 15.5 (20.43) | 8 | 3.91 (5.04) | 0.08 | 17 | 10.05 (16.0) |

SD: standard deviation; p value for Mann-Whitney U tests (continuous variables) and for Fisher's Exact tests (categorical data). Bold face values indicate statistical significances, specific. Casein/ALA/BLG IL-4 T-cells: number of casein/ALA/BLG specific IL-4 secreting T-cells for 300,000 lymphocytes. Casein/ALA/BLG IL-13 T-cells: number of casein/ALA/BLG specific IL-13 secreting T-cells for 300,000 lymphocytes. IgE: total immunoglobulin E (kU/L). sIgE: specific immunoglobulin E (kU/L). sIgG4: specific immunoglobulin G4 (mg/L)

b—Quantification of Circulating Cow's Milk Proteins Specific IL-4 and IL-13 Secreting T-Cells in CMA and Non-CMA Children.

The numbers of circulating cow's milk proteins specific IL-4 and IL-13 secreting T-cells between non-CMA children and CMA children were compared. The mean number of casein-specific IL-4 secreting T-cells was higher in CMA children than in non-CMA children (p=0.009; see FIG. 6A) and the mean number of casein-specific IL-13 secreting T-cells was higher in the CMA group (p=0.004; see FIG. 6B).

In the same manner, the mean ratios of serum levels of casein-specific IgE/total IgE and casein-specific IgE/IgG4 were also higher in the CMA group (p=0.02 and p=0.001 respectively).

In contrast, the mean numbers of α-lactalbumin-specific IL-13 or IL-4 secreting T-cells and β-lactoglobulin-specific IL-13 or IL-4 secreting T-cells were similar in the two groups (not shown).

C—Association Between the Number of Cow's Milk Proteins Specific IL-4 and IL-13 Secreting T-Cells and the Cumulative Reactive Dose.

The numbers of casein-specific IL-4 secreting T-cells and casein-specific IL-13 secreting T-cells were negatively correlated with the cow's milk cumulated dose tolerated (p=0.0009, r=−0.22 (and p=0.003, r=−0.58 respectively) (see FIG. 7).

In the same way, casein specific IgE/total IgE ratios and casein specific IgE/IgG4 ratios were also negatively correlated with the cumulated cow's milk dose tolerated in dose dependent manner (p=0.008, r=−0.53 and p=0.0004, r=−0.69 respectively).

Using an univariate linear regression model we found that the higher the frequency of casein-specific IL-13 and IL-4 secreting T-cells, the lower the cumulated cow's milk dose tolerated during the food challenge (p=0.01 and p<0.0001 respectively) (see Table 4).

TABLE 4

Association between CMP cumulated dose tolerated and different biological parameters.

|  | β | 95% confidence limits | p-value* |
| --- | --- | --- | --- |
| Casein sIgE | −0.39 | −0.85-0.07 | 0.1 |
| Casein sIgE/IgE | −406.2 | −654--158.5 | p = 0.001 |
| ALA sIgE/IgE | −1045.42 | −1684.55--406.3 | p = 0.001 |
| BLG sIgE/IgE | −562.07 | −1451.15; 327.01 | 0.22 |
| Casein sIgE/IgG4 | −62.7 | −173.9-48.55 | p = 0.3 |
| ALA sIgE/IgG4 | −71.9 | −196.2-52.5 | p = 0.3 |
| BLG sIgE/IgG4 | −1771.36 | (−3793.44-250.7) | p = 0.09 |
| Casein IL-4 T-cells | −3.44 | (−4.96--1.92) | p < 0.001 |
| ALA IL-4 T-cells | −1.5 | (−10.82--7.8) | p = 0.8 |
| BLG IL-4 T-cells | −7.7 | (−17.3-2.00) | p = 0.12 |
| Casein IL-13 T-cells | −1.4 | (−2.36--0.34) | p = 0.009 |

TABLE 4-continued

Association between CMP cumulated dose tolerated and different biological parameters.

|  | β | 95% confidence limits | p-value* |
|---|---|---|---|
| ALA IL-13 T-cells | −0.74 | (−2.24; 0.77) | 0.34 |
| BLG IL-13 T-cells | −1.79 | (−3.71; 0.14) | 0.07 |

Regression coefficients and confidence intervals provided by the univariate linear regression models allowed estimating the changes in cumulated dose tolerated quantity (mL) for an increase of 1 (UNIT) in each immunologic parameter.
Boldface values indicate statistical significance.
Casein/ALA/BLG IL-4 T-cells: number of casein/ALA/BLG specific IL-4 secreting T-cells for 300,000 lymphocytes.
Casein/ALA/BLG IL-13 T-cells: number of casein/ALA/BLG specific IL-13 secreting T-cells for 300,000 lymphocytes.
IgE: total immunoglobulin E (kU/L),
sIgE: specific immunoglobulin E (kU/L),
sIgG4: specific immunoglobulin G4 (mg/L).

d—ROC Curves and ELISpot Cut-Points

Considering these results, quantification of the frequency of casein-specific IL-4 and IL-13 secreting T-cells appeared to be suitable for the biological diagnosis of CMA.

In order to identify which test would show the best specificity and the best sensitivity for the diagnosis of cow's milk proteins allergy, receiver operating characteristic (ROC) curves were generated. Area under the curve (AUC) was 0.94 (95% CI, 0.81-1.00) for the frequency of casein-specific IL-13 and 0.87 (95% CI, 0.62-1.00) for the frequency of casein-specific IL-4 secreting T-cells.

Combining casein-specific IL-13 and casein-specific IL-4 secreting T-cells frequencies, we found the highest AUC (0.98, 95% CI, 0.90-1.0). As shown in Table 5 below, when using a clinical decision point of 10 casein-specific IL-4 and 12 casein-specific IL-13 secreting T-cells, a specificity of 80% and a sensitivity of 100% could be achieved, with a predictive positive value of 89% and a predictive negative value approaching 100%.

According to a correlation analysis, only one patient (whose casein-specific IgE level was as low as 0.43 KU/L) was out of the 95% prediction limits.

Furthermore, AUC was 0.81 (95% CI, 0.07-0.1) for casein specific IgE and 0.86 (95% CI, 0.63-1.0) for casein specific IgE/IgG4. When using a clinical decision point of 64.5 kU/L, a specificity of 100% and a sensitivity of 27% could be achieved, with a predictive positive value of 100% but a predictive negative value of 53% (see Table 5).

TABLE 5

Sensitivity, specificity, positive and negative predictive values for different cut-points (all the values are expressed as a percentage).

| Positivity Cut-off | Se | Spe | PPV | NPV |
|---|---|---|---|---|
| Casein IL-13 T-cells = 5 | 89 | 75 | 73 | 90 |
| Casein IL-13 T-cells = 12 | 10 | 58 | 64 | 100 |
| Casein IL-4 T-cells = 10 | 100 | 83 | 89 | 100 |
| Casein IL-4 T-cells = 10 + Casein IL-13 T-cells = 12 | 100 | 80 | 89 | 100 |
| Casein sIgE = 50.5 | 27 | 92 | 80 | 50 |
| Casein sIgE = 64.5 | 27 | 100 | 100 | 53 |
| Casein sIgE/IgG4 = 0.0015 | 60 | 100 | 100 | 75 |
| Casein sIgE/IgG4 = 0.0032 | 80 | 92 | 89 | 85 |
| Casein sIgE/IgG4 = 0.0011 | 100 | 67 | 71 | 100 |

Casein IL-4 T-cells: number of casein specific IL-4 secreting T-cells for 300,000 lymphocytes.
Casein IL-13 T-cells: number of casein specific IL-13 secreting T-cells for 300,000 lymphocytes.
Se: sensitivity,
Spe: specificity,
PPV: predictive positive value,
NPV: negative predictive value.

Example 6

Assessment of the Efficiency of Allergen-Specific Immunotherapy (AIT) Against House Dust Mite 1—Materials and Methods a—Study Design The study protocol was approved by the Ile de France 2 ethics committee and all parents and children over 11 years gave written informed consent. 15 asthmatic children mono-sensitized to *Dermatophagoides pteronyssinus* were recruited. Diagnosis was based on clinical symptoms and serological results.

TABLE 6

Clinical and biological characteristics on day 0 before starting AIT of patients responding and not responding to the desensitizing treatment. Values are given as mean (standard deviation) except if differently notified.

|  | Responders | Non responders |
|---|---|---|
| n | 9 | 6 |
| Male/female | 7/2 | 4/2 |
| age | 10 (3) | 7 (8) |
| Controlled with low doses ICS asthma (n) | 9 | 5 |
| Moderate to severe/intermittent to mild persistent rhinitis (n) | 6/3 | 0/6 |
| Total IgE (KU/L) | 271 (168) | 382 (387) |
| D. pter IgE (KU/L) | 29 (27) | 49 (35) |
| Der p 1 IgE (KU/L) | 20 (29) | 34 (37) |
| HDM-specific IL-4 secreting T-cells/0.3M PBMC | 47 (30) | 21 (23) |
| HDM-specific IL-13 secreting T-cells/0.3M PBMC | 35 (26) | 22 (17) |
| HDM-specific IL-10 secreting T-cells/0.3M PBMC | 118 (141) | 118 (231) | b—Allergen-Specific Immunotherapy (AIT)

The standardized extract used was 100% *Dermatophagoides pteronyssinus* administered as a glycerinated solution (SLIT®, ALK-ABELLO).

Sublingual AIT was daily self-administered at home, including a 10 days induction phase followed by a maintenance phase. Successful AIT was defined by a clinical amelioration of the rhinitis ARIA score after 1 year treatment (rhinitis severity was categorized as intermittent to mild persistent and moderate to severe persistent rhinitis).

To be classified as a responder, children with initially intermittent to mild rhinitis should exhibit no rhinitis after 1 year AIT and children with initially moderate to severe persistent rhinitis should exhibit either intermittent to mild rhinitis or no rhinitis after 1 year AIT.

2—Results

Following 1 year of AIT, 9/15 children (60%) exhibited a clinical amelioration (responder group). In the other 6 children, no significant clinical response was observed (non-responders group, see Table 6).

In the responder group, the number of HDM-specific IL-4 secreting T-cells significantly decreased at 6 and 12 months after AIT (p=0.05 and 0.02 respectively; see FIG. 8A). Similar results were found with IL-13 responses (see FIG. 8B). At variance, in the non-responders group, no significant modification in the frequency of HDM-specific IL-4 and IL-13 secreting T-cells was observed.

After 12 months of AIT, the number of HDM-specific IL-4 secreting T-cells was lower in the responder than in the non-responders group (p=0.04, see FIG. 9A); a tendency that did not reach statistical significance was observed for IL-13 (p=0.09, see FIG. 9B).

No IFNγ secreting T-cells were detected either before or after 6 or 12 months of AIT.

3—Conclusion

These results show that circulating pathogenic HDM-specific Th2 lymphocytes decreased after effective sublingual immunotherapy and that the decrease in the number of HDM-specific Th2 lymphocytes correlated with clinical response. This latter finding has not been reported so far for HDM allergy.

To our knowledge this is the first report that enumeration of allergen-specific Th2 cells may be useful to monitor sublingual AIT The method used herein, allows for detecting cytokine secreting T-cells after a short incubation with the allergen. This method has several advantages. It does not need previous in vitro expansion with cognate antigen thereby representing a snapshot of the in vivo situation and favoring the detection of experienced activated and memory T-cells in the patient. Furthermore, the use of a crude preparation of allergens allows for identifying cells specific for different epitopes. Finally, this test enables the analysis of individuals regardless of their HLA haplotype.

Finally, detecting of circulating allergen-specific T cells by an appropriate method allows for monitoring desensitization that may result from an allergen-specific immunotherapy (AIT).

REFERENCES

Patent Reference

WO 02/073195

Non-Patent References

Bach J-F. 2012. Hypersensibilités non liées aux immunoglobulins E. *Immunologie*, 6ème edition, Médecine Sciences Publications; p. 301-318.
Delespesse G. 2012. Hypersensibilité liée aux immunoglobulins E. *Immunologie*, 6ème edition, Medecine Sciences Publications; p. 290-300.
Flinterman et al. 2006. J Allergy Clin Immunol, 117:448.
Taylor et al. 2004. Clin Exp Allergy, 34:689.

The invention claimed is:

1. An in vitro method for measuring a number of IL-4 and/or IL-13 secreting memory T-cells contained in an isolated biological sample comprising memory T-cells, wherein said isolated biological sample is obtained from an individual having an IgE-dependent allergic disease selected from the group consisting of airborne allergies, food allergies and insect allergies, said method comprising at least the steps of:
    (a) contacting for a period of time comprised from about 12 to about 24 h, with an allergen capable of causing said IgE-dependent allergic disease, said isolated biological sample from said individual, in conditions suitable for said memory T-cells to secrete IL-4 and/or IL-13; and
    (b) measuring a number of IL-4 and/or IL-13 secreting memory T-cells contained in said biological sample.

2. The method according to claim 1 wherein step (a) is performed for a period of from about 15 h to about 22 h.

3. The method according to claim 1, further comprising a step of comparing said measured number of memory T cells with a reference value.

4. The method according to claim 1, wherein a number of memory T-cells secreting IL-4 and a number of memory T-cells secreting IL-13 are measured.

5. The method according to claim 1, wherein said measuring of the number of IL-4 and/or IL-13 secreting memory T cells is carried out by ELISpot.

6. A method for diagnosing and treating an IgE-dependent allergic disease to an allergen, in an individual suspected of having an IgE-dependent allergic disease, said method comprising at least the steps of:
    (a) contacting for a period of time comprised from about 12 to about 24 h, with an allergen capable of causing said IgE-dependent allergic disease, an isolated biological sample from said individual, said sample comprising memory T-cells, in conditions suitable for said memory T-cells to secrete IL-4 and/or IL-13;
    (b) measuring a number of IL-4 and/or IL-13 secreting memory T-cells contained in said biological sample;
    (c) comparing said measured number of memory T-cells with a reference value;
    (d) determining said individual has said IgE-dependent allergic disease when the measured number of memory T-cells is higher than said reference value; and
    (e) treating said individual determined in step (d) to have said IgE-dependent allergic disease with an immunotherapy.

7. The method according to claim 6, wherein step (a) is performed for a period of from about 15 h to about 22 h.

8. The method according to claim 6, wherein a number of memory T-cells secreting IL-4 and a number of memory T-cells secreting IL-13 are measured.

9. The method according to claim 6, wherein said measuring of the number of IL-4 and/or IL-13 secreting memory T-cells is carried out by ELISpot.

10. The method according to claim 6, wherein said IgE-dependent allergic disease is selected from the group consisting of airborne allergies, food allergies and insect allergies.

* * * * *